(12) United States Patent
Caetano et al.

(10) Patent No.: US 9,364,424 B2
(45) Date of Patent: *Jun. 14, 2016

(54) TOPICAL COSMETIC SKIN LIGHTENING COMPOSITIONS AND METHODS OF USE THEREOF

(71) Applicant: Stiefel Laboratories, Inc., New Castle, DE (US)

(72) Inventors: Joao Paulo Caetano, Sao Paulo (BR); Monica Alves Mariani De Oliveira, Sao Pauloa (BR)

(73) Assignee: Stiefel Laboratories, Inc., Wilmington, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/950,395

(22) Filed: Nov. 24, 2015

(65) Prior Publication Data

US 2016/0074315 A1  Mar. 17, 2016

Related U.S. Application Data

(63) Continuation-in-part of application No. 12/743,353, filed as application No. PCT/US2008/012952 on Nov. 19, 2008, now Pat. No. 9,241,893, which is a continuation-in-part of application No. PCT/US2007/024109, filed on Nov. 19, 2007.

(51) Int. Cl.

| A61K 8/97 | (2006.01) |
|---|---|
| A61Q 17/04 | (2006.01) |
| A61Q 19/08 | (2006.01) |
| A61Q 19/02 | (2006.01) |
| A61K 8/35 | (2006.01) |
| A61K 8/37 | (2006.01) |
| A61K 8/49 | (2006.01) |

(52) U.S. Cl.
CPC ... *A61K 8/97* (2013.01); *A61K 8/35* (2013.01); *A61K 8/355* (2013.01); *A61K 8/37* (2013.01); *A61K 8/496* (2013.01); *A61Q 17/04* (2013.01); *A61Q 19/02* (2013.01); *A61Q 19/08* (2013.01)

(58) Field of Classification Search
CPC ........... A61K 8/97; A61K 8/35; A61K 8/355; A61K 8/37; A61K 8/496; A61Q 17/04; A61Q 19/08; A61Q 19/02
See application file for complete search history.

(56) References Cited

U.S. PATENT DOCUMENTS

| 5,609,875 A | 3/1997 | Hadas |
| 6,090,369 A | 7/2000 | Stewart |
| 2001/0016213 A1 | 8/2001 | Singh-Verma |
| 2003/0198612 A1 | 10/2003 | Chaudhuri et al. |
| 2004/0028642 A1 | 2/2004 | Hansenne et al. |
| 2004/0175439 A1 | 9/2004 | Cyr |
| 2005/0163731 A1* | 7/2005 | Pelisson ............... A61K 8/347 424/59 |
| 2006/0018867 A1 | 1/2006 | Kawasaki et al. |
| 2006/0280704 A1 | 12/2006 | John |
| 2007/0020203 A1* | 1/2007 | Chaudhuri ............ A61K 8/675 424/59 |
| 2007/0122492 A1 | 5/2007 | Behr |
| 2008/0050459 A1 | 2/2008 | Elie et al. |

FOREIGN PATENT DOCUMENTS

| FR | WO2005/063191 | * 7/2005 | ............... A61K 7/48 |
| JP | 01-311011 A | 12/1989 | |
| JP | 06-271442 A | 9/1994 | |
| JP | 09-077638 A | 3/1997 | |
| JP | 2003-063925 A | 3/2003 | |
| JP | 2003-081749 A | 3/2003 | |
| JP | 2004-352697 A | 12/2004 | |
| JP | 2005-139070 A | 6/2005 | |
| WO | WO 2003/059313 A1 | 7/2003 | |
| WO | WO 2005/025532 A1 | 3/2005 | |
| WO | WO 2005/063191 A1 | 7/2005 | |
| WO | WO 2005/067885 A1 | 7/2005 | |
| WO | WO 2006/053912 | 5/2006 | |
| WO | WO 2007/107268 A1 | 9/2007 | |

OTHER PUBLICATIONS

Halder, et al. Skin Therapy Letter, 9(6): 1 (2004).
Masato Suzuki (Editorial Supervisor), Functional Cosmetics III, CMC Limited, Jan. 1, 2000, pp. 27-35 (in Japanese).
Masato Suzuki (Editorial Supervisor), Functional Cosmetics III, CMC Limited, Jan. 1, 2000 (English translation).

* cited by examiner

*Primary Examiner* — Sean Basquill
(74) *Attorney, Agent, or Firm* — Dara L. Dinner; Theodore R. Furman

(57) ABSTRACT

Topical cosmetic compositions are provided that can comprise a *Phyllanthus* extract, a *Bellis* extract, and a licorice (*Glycyrrhiza*) extract. These compositions are used for topical cosmetic applications, particularly to lighten skin. Methods for lightening skin are also provided and can comprise topically administering a therapeutically effective amount of a topical cosmetic composition comprising a *Phyllanthus* extract, a *Bellis* extract, and a licorice extract, to skin of a subject in need thereof.

17 Claims, 5 Drawing Sheets

Fig. 5 a & b. Photographic Register: Hydroquinone at T0 (day 0) and T21(day 21)

Fig. 5 c & d. Photographic Register: New Formulation at T0 and T21

Fig. 5 e & f. Photographic Register: Control at T0 and T21

TOPICAL COSMETIC SKIN LIGHTENING COMPOSITIONS AND METHODS OF USE THEREOF

FIELD OF THE INVENTION

The presently described subject matter relates to topical cosmetic or dermatological compositions comprising plant extracts. These compositions are used for topical cosmetic applications, particularly to treat undesired skin pigmentation.

BACKGROUND OF THE INVENTION

Topical cosmetic skin lightening compositions that are safe and effective are particularly desirable for treating undesirable skin pigmentation, including for example, regional hyperpigmentation caused by melanocytic hyperactivity such as idiopathic melasma occurring during pregnancy (mask of pregnancy or chloasma) or secondary to estrogen-progesterone contraception; local hyperpigmentation caused by benign melanocytic hyperactivity and proliferation such as lentigo senilis, known as liver spots; accidental hyperpigmentation such as post-lesional photosensitization and scarring; skin ageing (for example lentigines seniles); and certain forms of leukoderma such as vitiligo where, if the injured skin cannot be repigmented, the residual zones of normal skin are lightened or depigmented to impart a homogeneous color to the entire skin.

Several active ingredients and preparations that lighten skin, i.e., counteract skin pigmentation, are currently known. These products that are currently used contain hydroquinone, but such products have recently been deemed unacceptable for toxicological reasons. In fact, RDC 215 forbids the use of hydroquinone in cosmetic products after December, 2007.

U.S. Published Patent Application No. 2008/0050459 describes a cosmetic composition comprising an extract of *Phyllanthus Embilica*, an extract of *Bellis Perrenis*, an extract of *Glycyrrhiza Glabra*, and requiring at least one oligopeptide to achieve its cosmetic effect for the combined cosmetic treatment of fine lines and wrinkles, and/or skin brightening. Suitable oligopeptides are described as those having a suitable molecular weight so that they are able to act as carriers of *Phyllanthus Embilica* extract and penetrate skin to maximize the efficacy. The only oligopeptides described in the publication for achieving the cosmetic composition are oligopeptide-4 (pro-collagen oligopeptide) and oligopeptide-5 (pro-elastin oligopeptide).

There remains a need in the art for improved topical cosmetic compositions containing agents that safely and effectively lighten skin.

SUMMARY OF THE INVENTION

The present subject matter relates generally to topical cosmetic compositions useful for treating various skin disorders or conditions associated with undesired skin pigmentation. Further, the present subject matter relates to topical cosmetic compositions useful for cosmetic lightening of skin areas whose pigmentation is adequate for the individual skin type.

In an embodiment, the present subject matter relates to a topical cosmetic composition, comprising, consisting essentially of, or consisting of a *Phyllanthus* extract; a *Bellis* extract; and a licorice extract. In one embodiment, the cosmetic composition does not comprise at least one oligopeptide. In another embodiment, the cosmetic composition does not comprise at least one oligopeptide that is not normally present in *Phyllanthus* extract, *Bellis* extract, or licorice extract. In a further embodiment, the cosmetic composition does not comprise oligopeptide-4 (pro-collagen oligopeptide) or oligopeptide-5 (pro-elastin oligopeptide). In another embodiment, the cosmetic composition does not comprise at least one oligopeptide having a suitable molecular weight so that it is able to act as carrier of *Phyllanthus Embilica* extract and penetrate skin to maximize the efficacy.

In an embodiment, the present subject matter relates to a topical cosmetic composition, comprising, consisting essentially of, or consisting of a *Phyllanthus embilica* extract; a *Bellis perennis* extract; and a licorice extract.

In another embodiment, the present subject matter relates to a topical cosmetic composition, comprising, consisting essentially of, or consisting of a skin-lightening active component comprising, consisting essentially of, or consisting of a *Phyllanthus* extract, a *Bellis* extract, and a licorice extract; at least one sunscreen; and a cosmetically acceptable carrier.

In another embodiment, the present subject matter relates to a topical cosmetic composition, comprising, consisting essentially of, or consisting of a skin-lightening active component comprising, consisting essentially of, or consisting of a *Phyllanthus embilica* extract, a *Bellis perennis* extract, and a licorice extract; at least one sunscreen; and a cosmetically acceptable carrier.

In an embodiment, the present subject matter relates to a topical cosmetic composition, comprising, consisting essentially of, or consisting of a skin-lightening active component comprising, consisting essentially of, or consisting of a *Phyllanthus* extract, a *Bellis* extract, and a licorice extract; and a non-skin lightening component comprising at least one sunscreen.

In an embodiment, the present subject matter relates to a topical cosmetic composition, comprising, consisting essentially of, or consisting of a skin-lightening active component comprising, consisting essentially of, or consisting of a *Phyllanthus embilica* extract, a *Bellis perennis* extract, and a licorice extract; and a non-skin lightening component comprising at least one sunscreen.

In another embodiment, the present subject matter relates to a method of lightening skin pigmentation in a subject, comprising topically administering to skin of a subject in need thereof, a therapeutically effective amount of a topical cosmetic composition in accordance with the presently described subject matter.

In yet another embodiment, the present subject matter relates to a method of treating a skin disorder or condition in a subject, comprising topically administering to skin of a subject in need thereof a therapeutically effective amount of a topical cosmetic composition in accordance with the presently described subject matter.

DETAILED DESCRIPTION

Definitions

Figure 1:
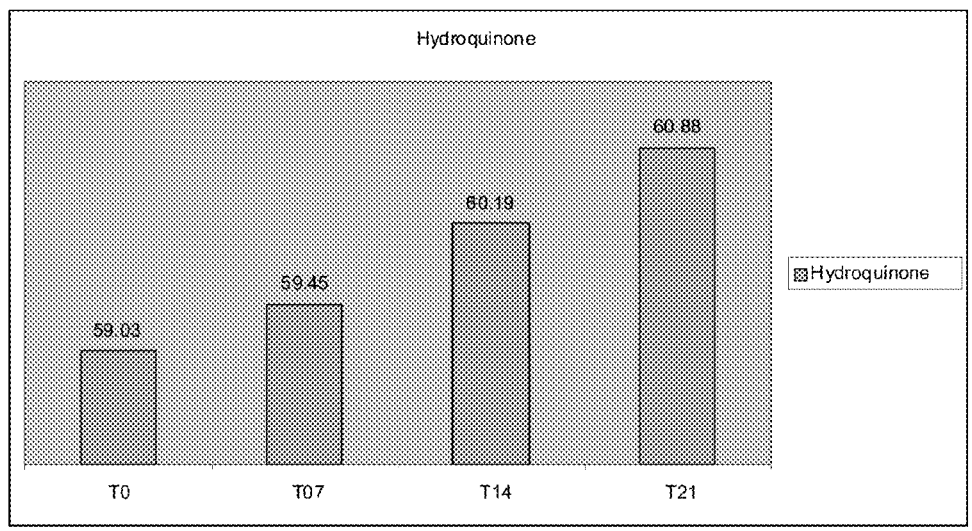
FIG. 1 illustrates progressive lightening over time that becomes statistically significant after 21 days for Site B treated with 2% hydroquinone.

As used herein, the terms "administering", "administration", and like terms refer to any method which, in sound medical or cosmetic practice, delivers the composition to a subject in such a manner as to provide a positive effect on a dermatological disorder, condition, or appearance. The compositions can be administered such that they cover the entire area to be treated.

As used herein "aqueous solvent" refers to a solvent such as water or containing water. Other dissolved components may be present in small amounts, such as, for example, salts, buffers, and other components understood by one of ordinary skill in the art to be optionally present in an aqueous solution.

"Anhydrous formulation" refers to any formulation of the present topical cosmetic composition that does not contain water.

"Cosmetically acceptable" refers to a non-toxic, inert, and/or physiologically compatible composition.

As used herein, the phrases an "effective amount" or a "therapeutically effective amount" of an active agent or ingredient, which are synonymous herein, refer to an amount of the active agent sufficient enough to have a positive effect on the area of application. Accordingly, these amounts are sufficient to modify the skin disorder, condition, or appearance to be treated but low enough to avoid serious side effects, within the scope of sound medical or dermatological advice.

As used herein, "epithelium" or "epithelial" refers to the layer of cells forming the epidermis of the skin and the surface layer of mucous and serous membranes. Epithelial cells have the general functions of protection, absorption, and secretion. Epithelial cells are often in close proximity to blood vessels, although generally lacking in a direct blood supply.

As used herein, "extract" refers to one or more components isolated from a plant source in a fluid or powder form. The plant source can comprise or consist of the entire plant or one or more parts of the plant, for example, the plant fruit, flower, root, leaves, stems, and/or bark. A fluid or liquid extract can be dried, for example, spray dried or desiccated, to form a powder. The extract can be a mixture of one or more components from a plant in a fluid and/or powder form.

By "non-skin lightening" is meant any compound, substance or composition; or agent; or component comprising, consisting essentially of, or consisting of one or more agents, substances, compounds and compositions, which upon topical application to skin does not depigment or lighten the skin. Such agents can include, for example, one or more active agents, for example, a sunscreen, an anti-acne agent, an anti-microbial agent, an anti-wrinkle agent, an anti-atrophy agent, an anti-inflammatory agent, and an optical brightener; and/or one or more cosmetically acceptable excipients, for example, a thickener, a chelating agent, a moisturizer, an emollient, a humectant, a gelling agent, a pH adjuster, a surfactant, a stabilizer, a vitamin, a penetration enhancer, a perfume, a coloring agent, and a solvent; and/or combinations thereof; as described herein.

As used herein, "pharmaceutically acceptable free bases, salts, esters, or solvates" refers to free bases, salts, esters, or solvates of subject compound(s) which possesses the same pharmacological activity as the subject compound(s) and which are neither biologically nor otherwise undesirable. A salt, ester, or solvate can be formed with, for example, organic or inorganic acids. Water or oil-soluble or dispersible products are thereby obtained.

As used herein, a "penetration enhancer" refers to a compound, substance or composition that reversibly reduces the barrier resistance of the horny layer of the skin, allowing an active agent to reach the living tissues at a greater rate.

As used herein, a "pH adjuster" or "pH modifier" refers to a specific pH adjusting agent added to a composition to convey a certain designated pH to the composition.

As used herein, "oligopeptide" refers to a peptide having a suitable molecular weight so that it is able to act as a carrier of *Phyllanthus Embilica* extract and penetrate skin. Oligopeptides that might act as carriers of *Phyllanthus Embilica* extract and penetrate skin include oligopeptide-4 (pro-collagen oligopeptide) and oligopeptide-5 (pro-elastin oligopeptide). As used herein, "oligopeptide" does not refer to any peptide that is normally present in *Phyllanthus* extract, *Bellis* extract, or licorice extract. It is noted that in an embodiment of the present subject matter, the cosmetic composition does not comprise at least one oligopeptide that is not normally present in *Phyllanthus* extract, *Bellis* extract, or licorice extract.

As used herein, "serum" refers to a hydrophilic liquid formulation. A serum may optionally be free from one or more of an emollient, a wax and a silicone.

As used herein, "skin lightening agent" refers to any compound, substance, or composition which upon topical application to skin lightens or depigments the skin. Such skin lightening agents can include, but are not limited to, pigmentation inhibitors, tyrosinase inhibitors, and melanocyte melanogenesis inhibitors.

As used herein, "subject" or "individual" or "animal" or "patient" or "mammal," refers to any subject, particularly a mammalian subject, for whom diagnosis, prognosis, or therapy is desired, for example, a human.

As used herein, "synergistic skin lightening system" or "synergistic skin lightening component" refers to a skin lightening active component comprising, consisting essentially of, or consisting of a *Phyllanthus embilica* extract, a *Bellis perennis* extract, and a licorice extract, that exhibits synergistic skin lightening efficacy as compared to the skin lightening efficacy of each individual skin lightening active agent. In this regard, the combination of these ingredients provides a greater than additive skin lightening effect.

As used herein, a "treatment" or "treating" of a skin disease, disorder, or condition encompasses alleviation of at least one symptom thereof, a reduction in the severity thereof, or the delay, prevention, or inhibition of the progression thereof. Treatment need not mean that the disease, disorder, or condition is totally cured. A useful composition herein needs only to reduce the severity of a skin disease, disorder, or condition, reduce the severity of symptoms associated therewith, provide improvement to a patient's quality of life, or delay, prevent, or inhibit the onset of a skin disease, disorder, or condition.

It is noted that, as used in this specification and the appended claims, the singular forms "a," "an" and "the" include plural references unless the context clearly dictates otherwise.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Topical Cosmetic Compositions

The present subject matter relates to a topical cosmetic composition, comprising, consisting essentially of, or consisting of a *Phyllanthus* extract; a *Bellis* extract; and a licorice extract.

Primary Skin Lightening Active Agents

In accordance with the presently described subject matter, the present topical cosmetic compositions can comprise or consist of a *Phyllanthus* extract, i.e., *Phyllanthus embilica* extract; a *Bellis* extract, i.e., a *Bellis perennis* extract; and a licorice extract.

"*Phyllanthus* extract" means an extract obtained from the fruit of a member of the *Phyllanthus* genus, including for example, of *Phyllanthus embilica, Phyllanthus niruri* L., *Phyllanthus elegans* Wall, *Phyllanthus iniruri, Phyllanthus reticulatus, Phyllanthus urinaria* L., *Phyllanthus reticulatus* Poir, *Phyllanthus conami* Sw, *Phyllanthus lathyroides* H. B. K., *Phyllanthus casticum* Soy-Will, and *Phyllanthus madagascariensis. Phyllanthus* extract is a safe and effective natural antioxidant.

"*Phyllanthus embilica* extract" means a standardized extract of *Phyllanthus embilica*, including for example, EMBLICA® (Merck KGaA, Darmstadt, Germany and EM industries, Inc., USA, an affiliate of Merck KGaA). *Phyllanthus embilica* is also commonly known as "*Emblica officinalis* Gaertn" and is a member of the family "Euphorbiaceae." *Phyllanthus embilica* is a very rich source of vitamin C, having an ascorbic acid content in the range from 1000 to 1800 mg per 100 grams of fruit. *Phyllanthus embilica* extract is a safe and effective natural antioxidant that has no pro-oxidation activity and can exhibit dual functionality, i.e., chelation and antioxidant. Unlike most antioxidants that go from an active to an inactive form, *Phyllanthus embilica* extract can exhibit a cascading effect that provides long-lasting and stable antioxidant activity. *Phyllanthus embilica* extract can be produced by extracting premium quality fruits using a water-based process as described in U.S. Pat. No. 6,124,268, incorporated herein by reference in its entirety. *Phyllanthus embilica* extract typically contains low-molecular weight tannins, namely Emblicanin A and Emblicanin B, along with Pedunculagin and Punigluconin, Rutin and Gallo-ellagitannoids.

"*Bellis* extract" means an extract obtained from a member of the *Bellis* genus, including for example, the extract obtained from the flowers of a member of the *Bellis* genus, for example, from *Bellis perennis* flowers and/or from *Bellis rotundifolia* L. flowers. The *Bellis* extract can comprise or consist of one or more bioactive molecules including saponins (triterpene glycosides), polyphenols (phenolic acid), flavonoid glycosides, polysaccharides and inulin.

"*Bellis perennis* extract" means the extract obtained from *Bellis perennis* flowers that can comprise or consist of one or more bioactive molecules including saponins (triterpene glycosides), polyphenols (phenolic acid), flavonoid glycosides, polysaccharides and inulin. Suitable *Bellis perennis* extracts can include BELIDES® available from CLR Chemisches Laboratorium, Berlin, Germany. *Bellis perennis* is also commonly known as *Bellis alpina* Hegetschw., *Bellis hortensis* Mill., *Bellis hybrida* Ten., *Bellis integrifolia* DC., and *Bellis scaposa* Gilib.

"Licorice extract" means an extract obtained from a member of the *Glycyrrhiza* genus, for example obtained from the root of a member of the *Glycyrrhiza* genus. The genus "*Glycyrrhiza*" is a member of the family "Fabaceae." Suitable *Glycyrrhiza* extracts can include the oil soluble licorice extract available from Bioland, Korea. Other suitable *Glycyrrhiza* extracts can be obtained from one or more of the following members of the *Glycyrrhiza* genus including *Glycyrrhiza echinata* L. (Chinese licorice), *Glycyrrhiza glabra* L. (cultivated licorice), *Glycyrrhiza lepidota* L., *Glycyrrhiza glutinosa, polypodium Glycyrrhiza, Glycyrrhiza brachycarpa* Boiss., *Glycyrrhiza germanica* Tourn., *Glycyrrhiza glandulifera* Waldst. et Kit., *Glycyrrhiza hirsuta* L., *Glycyrrhiza laevis* Pall., *Glycyrrhiza officinalis* Lepech., *Glycyrrhiza pallida* Boiss., *Glycyrrhiza siliquosa* Tourn., *Glycyrrhiza violacea* Boiss., *Glycyrrhiza viscosa* Turcz. ex Ledeb., *Glycyrrhiza vulgaris* Gueldenst. ex Ledeb, *Liquiritia officinalis* Moench, and *Liquiritia officinarum* Medik.

In an embodiment, the present topical cosmetic composition can comprise, consist essentially of, or consist of a skin lightening active component that can comprise or consist of a *Phyllanthus* extract, a *Bellis* extract, and a licorice extract.

In an embodiment, the present topical cosmetic composition can comprise, consist essentially of, or consist of a skin lightening active component that can comprise or consist of a *Phyllanthus embilica* extract, a *Bellis perennis* extract, and a licorice extract.

In an embodiment, the present subject matter relates to a topical cosmetic composition wherein the total skin lightening active component is present in the topical cosmetic composition in an amount of from about 0.5% to about 43% by weight, from about 1% to about 30% by weight, from about 1.5% to about 23% by weight, from about 1.5% to about 15% by weight, from about 3% to about 10% by weight, from about 6% to about 8% by weight, or about 7.05% by weight, based on the total weight of the composition.

In another embodiment, the present subject matter relates to a topical cosmetic composition wherein the *Phyllanthus* extract, for example, the *Phyllanthus embilica* extract, is present in the topical cosmetic composition in an amount of from about 0.1% to about 8% by weight, from about 0.25% to about 4% by weight, from about 0.5% to about 3% by weight, from about 0.5% to about 2% by weight, from about 1% to about 2% by weight, or about 2% by weight, based on the total weight of the composition.

In a further embodiment, the present subject matter relates to a topical cosmetic composition wherein the *Bellis* extract, for example, the *Bellis perennis* extract, is present in the topical cosmetic composition in an amount of from about 0.5% to about 30% by weight, from about 1% to about 20% by weight, from about 2% to about 10% by weight, from about 3% to about 7% by weight, from about 4% to about 6% by weight, or about 5.0% by weight, based on the total weight of the composition.

In yet another embodiment, the present subject matter relates to a topical cosmetic composition wherein the licorice extract is present in the topical cosmetic composition in an amount of from about 0.005% to about 5% by weight, from about 0.01% to about 2% by weight, from about 0.01% to about 1% by weight, from about 0.02% to about 0.08% by weight, from about 0.03% to about 0.07% by weight, or about 0.05% by weight, based on the total weight of the composition.

In another embodiment, the present subject matter relates to a topical cosmetic composition wherein the *Phyllanthus* extract, for example, the *Phyllanthus embilica* extract, is present in the topical cosmetic composition in an amount of from about 0.50 wt % to about 2 wt %; the *Bellis* extract, for example, the *Bellis perennis* extract, is present in the topical cosmetic composition in an amount of from about 1 wt % to about 20 wt %; and the licorice extract is present in the topical cosmetic composition in an amount of from about 0.01 wt % to about 1 wt %.

In yet another embodiment, the present subject matter relates to a topical cosmetic composition, wherein the *Phyllanthus embilica* extract is present in the topical cosmetic composition in an amount of about 2 wt %; the *Bellis perennis* extract is present in an amount of about 5 wt %; and the licorice extract is present in the topical cosmetic composition in an amount of about 0.05 wt %.

In an embodiment, the present subject matter relates to a topical cosmetic composition, comprising, consisting essentially of, or consisting of a skin-lightening active component comprising, consisting essentially of, or consisting of a *Phyllanthus* extract, for example, a *Phyllanthus embilica* extract; a *Bellis* extract, for example, a *Bellis perennis* extract; and a licorice extract; at least one sunscreen; and a cosmetically acceptable carrier. The cosmetically acceptable carrier can comprise or consist of one or more cosmetically acceptable excipients.

In another embodiment, the present subject matter relates to a topical cosmetic composition, comprising, consisting essentially of, or consisting of a skin-lightening active component comprising, consisting essentially of, or consisting of a *Phyllanthus* extract, for example, a *Phyllanthus embilica* extract; a *Bellis* extract, for example, a *Bellis perennis* extract; and a licorice extract; and a non-skin lightening component. The non-skin lightening component can comprise or consist of one or more of an active agent, for example, a sunscreen; a cosmetically acceptable carrier; and/or a cosmetically acceptable excipient, as described herein.

In a further embodiment, the present subject matter relates to a topical cosmetic composition in accordance with the subject matter described herein that can comprise one or more non-skin lightening active agents.

In yet another embodiment, the topical cosmetic composition and/or the cosmetically acceptable carrier and/or one or more cosmetically acceptable excipients, can be free from any skin lightening agents other than a *Phyllanthus* extract, for example a *Phyllanthus embilica* extract; a *Bellis* extract, for example, a *Bellis perennis* extract; and licorice extract. The topical cosmetic composition and/or the cosmetically acceptable carrier and/or one or more cosmetically acceptable excipients, can be free from any plant derived skin lightening agents other than a *Phyllanthus* extract, for example a *Phyllanthus embilica* extract; a *Bellis* extract, for example, a *Bellis perennis* extract; and licorice extract. The topical cosmetic composition and/or the cosmetically acceptable carrier and/or one or more cosmetically acceptable excipients can be free from any non-plant derived skin lightening agents.

In an embodiment, the present subject matter relates to a topical cosmetic composition, wherein the composition and/or a skin lightening active component and/or a non-skin lightening component, does not comprise hydroquinone or a derivative thereof, and/or does not comprise a polyorganosiloxane-containing epsilon-polylysine compound, and/or does not comprise a flavan.

Synergistic Skin Lightening Component

In another embodiment, the present subject matter relates to a topical cosmetic composition that can comprise or consist of a synergistic skin lightening active component comprising, consisting essentially of, or consisting of a *Phyllanthus* extract, for example a *Phyllanthus embilica* extract; a *Bellis* extract, for example, a *Bellis perennis* extract; and licorice extract, wherein the synergistic skin lightening active component exhibits synergistic skin lightening efficacy as compared to the skin lightening efficacy of each individual skin lightening active agent.

In an embodiment, the present subject matter relates to a synergistic skin lightening component for use in a topical cosmetic composition comprising, consisting essentially of, or consisting of a *Phyllanthus* extract, for example a *Phyllanthus embilica* extract; a *Bellis* extract, for example, a *Bellis perennis* extract; and licorice extract.

In another embodiment, the present subject matter relates to a synergistic skin lightening component for use in a topical cosmetic composition comprising, consisting essentially of, or consisting of a *Phyllanthus* extract, for example a *Phyllanthus embilica* extract; a *Bellis* extract, for example, a *Bellis perennis* extract; and licorice extract, wherein the synergistic skin lightening component demonstrates enhanced skin lightening efficacy. The synergistic skin lightening component can be free from hydroquinone.

In an embodiment, the topical cosmetic composition in accordance with the presently described subject matter, can comprise or consist of a skin lightening active component that exhibits synergistic skin lightening efficacy.

In a further embodiment, the topical cosmetic composition in accordance with the presently described subject matter, can comprise or consist of a skin lightening active component that exhibits synergistic skin lightening efficacy, wherein the topical cosmetic composition is free from hydroquinone.

In an embodiment, the topical cosmetic composition or the synergistic skin lightening system, in accordance with the presently described subject matter, can comprise or consist of a skin lightening active component that exhibits synergistic skin lightening efficacy, wherein the topical cosmetic composition is free from hydroquinone and/or a flavan and/or a polyorganosiloxane-containing epsilon-polylysine compound.

Cosmetically Acceptable Carrier

Any non-toxic, inert, and effective topical cosmetically acceptable carrier may be used to formulate the compositions described herein. Well-known carriers used to formulate other topical therapeutic compositions for administration to humans are useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful cosmetically acceptable excipients, carriers and diluents include distilled water, physiological saline, Ringer's solution, dextrose solution, Hank's solution, and DMSO, which are among those suitable for use herein.

These additional other inactive components, as well as effective formulations and administration procedures, are well known in the art and are described in standard textbooks, such as *Goodman and Gillman's: The Pharmacological Bases of Therapeutics*, 8th Ed., Gilman et al. Eds. Pergamon Press (1990) and *Remington's Pharmaceutical Sciences*, 17th Ed., Mack Publishing Co., Easton, Pa. (1990), both of which are incorporated by reference herein in their entirety.

Sunscreens

In another embodiment, the present subject matter relates to a topical cosmetic composition that can comprise at least one sunscreen. The at least one sunscreen can be present in an amount of from about 0.5% to about 30% by weight based on the total weight of the topical cosmetic composition, from about 1% by weight to about 20% by weight, or from about 1% by weight to about 10% by weight based on the total weight of the composition.

Suitable sunscreens can include broad-spectrum sunscreens that protect against both UVA and UVB radiation, or sunscreen agents that protect against UVA or UVB radiation.

Non-limiting examples of suitable sunscreens include sunscreen agents that can comprise or consist of one or more of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropy dibenzoylmethane, 3-benzylidene camphor, 3-(4-methylbenzylidene) camphor, titanium dioxide, zinc oxide, silica, iron oxide, 4-N,N-(2-ethylhexyl)methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, dihydroxycinnamic acid, trihydroxycinnamic acid, diphenylbutadiene, stilbene, dibenzalacetone, benzalacetophenone, naphtholsulfonates, 2-naphthol-3,6-disulfonic, 2-naphthol-6,8-disulfonic acids, di-hydroxynaphthoic acid, o- and p-hydroxybiphenyldisulfonates, coumarin, diazoles, 2-acetyl-3-bromoindazole, phenyl benzoxazole, methyl naphthoxazole, various aryl benzothiazoles, quinine salts, quinoline derivatives, 8-hydroxyquinoline, 2-phenylquinoline, hydroxy- and methoxy-substituted benzophenones, uric, violuric acids, tannic acid, benzophenones, oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, octocrylene, 3-(4'-methylbenzylidene boman-2-one), terephthalylidene dicamphor sulfonic acid, 4-isopropyl-di-benzoyl-methane, butylmethoxydibenzoyl-methane, 2-hydroxy-4-methoxybenzo-phenone, 2-phenyl benzimidazole-5-sulfonic acid, octyldimethyl-p-aminobenzoicacid, octocrylene, 4-N,N-(2-ethylhexyl)methyl-aminobenzoic acid ester of 2,4-dihydroxybenzophenone, N,N-di-(2-ethylhexyl)-4-aminobenzoic acid ester with 4-hydroxydibenzoylmethane, 4-N,N-(2-ethylhexyl)-methylaminobenzoic acid ester of 4-(2-hydroxyethoxy)dibenzoylmethane, N,N-di-(2-ethylhexyl)-4-aminobenzoic acid ester of 2-hydroxy-4-(2-hydroxyethoxy)benzophenone, N,N-di-(2-ethylhexyl)-4-aminobenzoic acid ester of 4-(2-hydroxyethoxy) dibenzoylmethane, pharmaceutically or cosmetically acceptable salts thereof, and mixtures thereof.

In an embodiment, the present topical cosmetic compositions can comprise a sunscreen comprising or consisting of one or more of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

In an additional embodiment, the present topical cosmetic compositions can comprise a sunscreen comprising one or more of methylene bis-benzotriazolyl tetramethylbutylphenol (TINOSORB M available from CIBA), diethylamino hydroxybenzoyl hexyl benzoate, and coated zinc oxide, in an amount of from about 1% to about 20% by weight, from about 2% to about 10% by weight, or of about 5% by weight, based on the total weight of the composition. For example, the present topical cosmetic compositions can comprise a sunscreen comprising methylene bis-benzotriazolyl tetramethylphenol in an amount of from about 1% to about 20% by weight, from about 2% to about 10% by weight, or of about 5% by weight, based on the total weight of the composition In a further embodiment, the present topical cosmetic compositions can comprise a sunscreen comprising or consisting of one or more of ethylhexyl methoxycinnamate (available from BASF), isoamyl methoxycinnamate, homosalate ethyl hexyl salicilate, octocrylene, polysilicone-15, butyl methoxydibenzoylmethane, menthyl anthranilate, and ethylhexyl dimethyl PABA, in an amount of from about 1% to about 10%, from about 5% to about 9%, or of about 7.5% by weight, based on the total weight of the composition.

In an embodiment, the present topical cosmetic compositions can comprise one or more sunscreens in an amount of from about 0.5% by weight to about 30% by weight, from about 1% by weight to about 20% by weight, or from about 1% by weight to about 10% by weight based on the total weight of the composition.

In an embodiment, the at least one sunscreen can comprise or consist of a first sunscreen selected from the group consisting of methylene bis-benzotriazolyl tetramethylphenol, diethylamino hydroxybenzoyl hexyl benzoate, and coated zinc oxide; and a second sunscreen selected from the group consisting of ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA. The first sunscreen can be present in an amount of from about 1% to about 20% by weight, and the second sunscreen can be present in an amount of from about 1% to about 10% by weight, based on the total weight of the topical cosmetic composition. The first sunscreen can comprise or consist of methylene bis-benzotriazolyl tetramethylbutylphenol, and the second sunscreen can comprise or consist of ethylhexyl methoxycinnamate.

In an embodiment, the present subject matter relates to a topical cosmetic composition that has an SPF of greater than about 10, has an SPF of greater than about 15, an SPF of at least about 15, an SPF of about 15, an SPF of from about 10 to about 45, an SPF of from about 15 to about 45, or an SPF of from about 15 to about 25.

Aqueous Solvent

The present topical cosmetic compositions can additionally comprise an aqueous solvent. In an embodiment, the present compositions comprise an aqueous solvent, for example, water, in an amount of from about 5% to about 95% by weight, from about 10% to about 90% by weight, from about 25% to about 80% by weight, from about 55% to about 75% by weight, from about 60% to about 70% by weight, or about 63% by weight, based on the total weight of the composition.

Cosmetically Acceptable Excipients

In yet another embodiment, the present subject matter relates to a topical cosmetic composition that can comprise water and at least one cosmetically acceptable excipient. Suitable cosmetically acceptable excipients include those commonly known to one of ordinary skill in the art as useful in topical compositions.

In an embodiment, the at least one cosmetically acceptable excipient can comprise or consist of one or more members selected from the group consisting of an antioxidant, a chelating agent, a pH adjuster, an emollient, a thickening agent, gelling agent, free radical scavenger, a preservative, an emulsifier, a humectant, a moisturizer, a suspending agent, a surfactant, a stabilizer, a vitamin, a penetration enhancer, a perfume or fragrance, a coloring agent, fluid alkyl alcohols, polysiloxanes, modified polysiloxanes, and combinations thereof.

Antioxidants

The topical cosmetic compositions may optionally further comprise one or more anti-oxidants. Suitable anti-oxidants that can optionally be included in these compositions can comprise or consist of one or more of ascorbic acid, ascorbyl esters of fatty acids, magnesium ascorbyl phosphate, sodium ascorbyl phosphate, ascorbyl sorbate, tocopherol, tocopherol sorbate, tocopherol acetate, butylated hydroxy benzoic acid, thioglycolates, persulfate salts, 6-hydroxy-2,5,7,8-tetramethylchroman-2-carboxylic acid, lipoic acid, gallic acid, propyl gallate, uric acid, sorbic acid, lipoic acid, amines, N,N-diethylhydroxylamine, N-acetyl-L-cysteine, amino-guanidine, sulfhydryl compounds, glutathione, dihydroxy fumaric acid, lysine pidolate, arginine pilolate, nordihydroguaiaretic acid, bioflavonoids, curcumin, lysine, 1-methionine, proline, superoxide dismutase, silymarin, tea extracts, grape skin/seed extracts, melanin, rosemary extracts, derivatives thereof, and combinations thereof.

In an embodiment, the present topical cosmetic composition can include a suitable antioxidant that can comprise or consist of one or more of butylated hydroxytoluene, sodium metabissulfite, butylated hydroxyl anisol, ascorbic acid and derivatives thereof, a sulfite and derivatives thereof, an ester, and tocopherol acetate, for example, in an amount of from about 0.01% to about 0.5% by weight, of from about 0.01% to about 0.2% by weight, from about 0.02% to about 0.1% by weight, from about 0.03% to about 0.07% by weight, or about 0.05% by weight, based on the total weight of the composition. The present topical cosmetic composition can comprise sodium metabissulfite, for example, in an amount of from about 0.1% to about 0.5% by weight, from about 0.2% to about 0.4% by weight, or about 0.3% by weight, based on the total weight of the composition. In addition, the present topical cosmetic composition can comprise butylated hydroxytoluene, for example, in an amount of from about 0.01% to about 0.2% by weight, from about 0.02% to about 0.1% by weight, from about 0.03% to about 0.07% by weight, or about 0.05% by weight, based on the total weight of the composition. The present topical cosmetic composition can comprise an antioxidant that can comprise or consist of butylated hydroxytoluene and sodium metabissulfite, for example, in a combined amount of from about 0.01% to about 0.6% by weight, from about 0.2% to about 0.5% by weight, or about 0.35% by weight, based on the total weight of the composition.

The one or more antioxidants can be present in the topical cosmetic composition, for example, in an amount of from about 0.01% to about 0.6% by weight, from about 0.1% to about 0.5% by weight, or from about 0.2% to about 0.5% by weight, based on the total weight of the composition.

Chelating Agents

The present topical cosmetic compositions may optionally further comprise one or more chelating agents. Suitable chelating agents that can optionally be included in these compositions can comprise or consist of one or more of citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (Nitrilotriacetic Acid), HEDTA (N-(hydroxyethyl)-ethylenetriaminetriacetic acid), aminocarboxylates, dimercaperol (BAL), larixinic acid (Maltol), unidentate ligands (fluoride and cyanide ions), diphenylthiocarbazone, 0-phenanthroline, barium diphenylamine sulfonate, sodium glucoheptonate, 8-hydroxyquinoline, olefin complexes (such as dicyclopentadienyl iron), porphyrins, phosponates, pharmaceutically or cosmetically acceptable salts thereof, derivatives thereof, and mixtures thereof.

The present topical cosmetic composition can include one or more chelating agents present in an amount of from about 0.05% to about 1% by weight, from about 0.1% to about 0.5% by weight, or about 0.2% by weight, based on the total weight of the composition.

In an embodiment, the present topical cosmetic composition can include a chelating agent that can comprise or consist of one or more of disodium edetate, EDTA, disodium EDTA, trisodium EDTA, and tetrasodium EDTA, for example, in an amount of from about 0.2% to about 0.4% by weight, based on the total weight of the composition.

pH Adjusters

The present topical cosmetic compositions may optionally further comprise one or more pH adjusters. Suitable neutralizing pH adjusters that can optionally be included in these compositions can comprise or consist of one or more of inorganic hydroxides, inorganic oxides, inorganic salts of weak acids, derivatives thereof, and mixtures thereof.

Suitable inorganic hydroxides useful in this regard can comprise or consist of one or more of ammonium hydroxide, alkali metal hydroxide, alkaline earth metal hydroxides, derivatives thereof, and mixtures thereof.

Suitable inorganic hydroxides useful in this regard can comprise or consist of one or more of ammonium hydroxide, monovalent alkali metal hydroxides such as sodium hydroxide and potassium hydroxide, divalent alkali earth metal hydroxides such as calcium hydroxide and magnesium hydroxide, derivatives thereof, and mixtures thereof.

Suitable inorganic oxides useful in this regard can comprise or consist of one or more of magnesium oxide, calcium oxide, derivatives thereof, and mixtures thereof.

Suitable inorganic salts of weak acids useful in this regard can comprise or consist of one or more of ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and mixtures thereof.

In an embodiment, the present topical cosmetic composition can include a pH adjuster that can comprise or consist of one or more of triethanolamine, aminomethylpropanol, and sodium hydroxide. The pH adjuster can be present in the composition, for example, in an amount of from about 0.1% to about 1% by weight, from about 0.2% to about 0.9% by weight, or about 0.6% by weight, based on the total weight of the composition. The present topical cosmetic composition can comprise a pH in the range of from about 2.5 to about 8, or from about 3 to about 7.

Emollients

The present topical cosmetic compositions may further comprise an emollient. Suitable non-limiting examples of emollients useful in the present compositions include one or more of myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, a glycol, lecithin, and mixtures thereof.

In an embodiment, a suitable emollient can comprise or consist of one or more of glycerin; a glycol, for example, propylene glycol, butyleneglycol, and pentyleneglycol; cyclopentasiloxane dimethicone crosspolymer (DC9040 available from Dow Corning); cyclopentasiloxane PEG/PPG-18/18 dimethicone (DC5225C available from Dow Corning); and a silicon derivate. The emollient may be present in an amount of from about 1% to about 20% by weight, from about 2% to about 10% by weight, from about 3% to about 8% by weight, or about 4% by weight.

Thickening/Gelling Agents

The present topical cosmetic composition may optionally further comprise one or more thickening agents. Suitable thickening agents that can optionally be included in these compositions can comprise or consist of, but are not limited to, one or more of a cellulosic polymer, such as gum arabic, gum tragacanth, locust bean gum, guar gum, xanthan gum, cellulose gum, methylcellulose, hydroxyethylcellulose, hydroxypropylcellulose, and hydroxypropylmethylcellulose; sodium carbomer; carbomer; a polyacrylic polymer; an aqueous gelling agent, such as neutral, anionic, and cationic polymers; polymers, such as carboxy vinyl polymers, such as carboxypolymethylene; an acrylate copolymer; a polysorbate; a fatty alcohol, for example, cetyl alcohol and stearyl alcohol; glyceryl stearate; an alkyl derivate; and mixtures thereof. Suitable acrylate copolymers can comprise or consist of, but are not limited to, one or more of hydroxyethyl acrylate and sodium acryloyldimethyltaurate copolymer.

In an embodiment, a suitable thickening agent can comprise or consist of one or more of a fatty alcohol, for example, cetyl alcohol and stearyl alcohol; glyceryl stearate; an alkyl derivate; and combinations thereof; for example, present in an amount of from about 0.25% to about 4% by weight, from about 0.5% to about 3% by weight, from about 1% to about 2% by weight, or about 2% by weight, based on the total weight of the composition.

In an embodiment, a suitable thickening agent can comprise or consist of one or more of hydroxyethyl acrylate, sodium acryloyldimethyltaurate copolymer, squalane, polysorbate 60, a carbomer derivative, an acrylate, an acrylamide, xanthan gum, carrageenan gum, aluminium silicate, magnesium silicate, and a cellulose derivate, for example, present in an amount of from about 1% to about 10% by weight, from about 2% to about 8% by weight, from about 3% to about 7% by weight, or about 5% by weight, based on the total weight of the composition.

A suitable thickening agent can comprise or consist of hydroxyethyl acrylate, sodium acryloyldimethyltaurate copolymer, squalane, and polysorbate 60, for example, in an amount of from about 1% to about 10% by weight, or about 5% by weight, based on the total weight of the composition, which is available as SIMUGEL NS® from SEPPIC, Fairfield, N.J. This thickening agent can be used in the presently described topical cosmetic composition in combination with a further thickening agent, for example, cetyl alcohol, in an amount of from about 0.5% to about 2% by weight, or about 2% by weight, based on the total weight of the composition.

The one or more thickening agents can be present in the topical cosmetic composition in an amount of from about 0.25% to about 15% by weight, from about 1% to about 12% by weight, from about 4% to about 10% by weight, from about 5% to about 9% by weight or about 7% by weight, based on the total weight of the composition.

Free Radical Scavengers

The described topical cosmetic compositions may optionally further comprise an effective amount of a free radical scavenger. By "effective amount" is meant an amount sufficient to provide protection when the composition is properly applied, but not so much as to cause any side effects or adverse skin reactions; generally from about 0.1% to about 20%, or from about 1% to about 5%, of the composition. Examples of such free radical scavengers include but are not limited to, ascorbic acid (Vitamin C) and its salts and derivatives (e.g., magnesium ascorbyl phosphate, sodium ascorbyl phosphate, Ascorbyl palmitate, etc.), tocopherol (Vitamin E), tocopherol esters (e.g., tocopheryl acetate, tocopheryl succinate, tocopheryl sorbate), butylated hydroxy benzoic acids and their salts, 6-hydroxy-2,5,7,8-tetramethylchroman-2-carboxylic acid (commercially available under the tradename TROLOX R®), gallic acid and its alkyl esters (propyl gallate), uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxyfumaric acid and its salts. Additionally, catechins and polyphenols (e.g., those found in green tea extract) and flavonoids (e.g., isoflavones such as genistein, and daidxein which are found in soy extracts, flavones, chalcones, flavanones, coumarins, etc.) can be used.

Preservatives

The described topical cosmetic compositions may optionally further comprise one or more preservatives. Suitable preservatives that can optionally be included in these compositions can comprise or consist of, but are not limited to, one or more of propylene glycol, glycerol, butylene glycol, pentylene glycol, hexylene glycol, sorbitol, benzyl alcohol, derivatives thereof, and mixtures thereof.

In an embodiment, a suitable preservative can comprise or consist of one or more of phenoxyethanol, methylisothiazolinone, phenoxyethanol, a paraben, imidazolynidyl urea, and combinations thereof. Additionally, the preservative can be present in an amount of from about 0.05% to about 1.5% by weight, from about 0.1% to about 1% by weight, from about 0.1% to about 0.6% by weight, or of about 0.6% by weight, based on the total weight of the composition. In a further embodiment, a suitable preservative can comprise or consist of phenoxyethanol and methylisothiazolinone, for example, NEOLONE PE® which is a formaldehyde-free broad-spectrum bactericide based on methylisothiazolinone and phenoxyethanol Rohm & Haas, Philadelphia, Pa.

Emulsifiers

The topical cosmetic compositions may optionally further comprise one or more emulsifiers. Suitable emulsifiers that can optionally be included in these compositions can comprise or consist of any of a wide variety of nonionic, cationic, anionic, zwitterionic and amphoteric emulsifiers.

Suitable non-limiting examples of emulsifiers useful in this regard can include emulsifiers that can comprise or consist of one or more of glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, derivatives thereof, and mixtures thereof.

In an embodiment, the present topical cosmetic composition can include an emulsifier that can comprise or consist of one or more of a $C_{14-22}$ alcohol and a $C_{12-20}$ alkyglucoside, for example, MONTANOV L® which is a combination of fatty alcohols and alkyl glucosides available fro SEPPIC, Fairfield, N.J. Suitable emulsifiers can include one or more of potassium cetyl phosphate, an alkyl phosphate, PEG 100-glyceryl stearate and blends thereof, an ethoxylated fatty alcohol in combination with one or more fatty alcohols and/or glyceryl stearates, and an alkyl sulphate.

In an embodiment, the present topical cosmetic skin-lightening compositions can comprise of from about 0.5% to about 10% by weight of an emulsifier, from about 1% to about 5% by weight, from about 1.5% to about 3.5% by weight, or about 2% by weight emulsifier, based on the total weight of the composition.

Humectants

The present topical cosmetic compositions may further comprise a humectant. Suitable non-limiting examples of humectants useful in the present compositions include glycerin, butylene glycol, propylene glycol, sorbitol, and triacetin.

Moisturizers

The topical cosmetic compositions may optionally further comprise one or more moisturizers. Suitable moisturizers can comprise or consist of, but are not limited to, one or more of glycerin, pentylene glycol, butylene glycol, polyethylene glycol, sodium pyrrolidone carboxylate, alpha-hydroxy acids, beta-hydroxy acids, polyhydric alcohols, ethoxylated and propoxylated polyols, polyols, polysaccharides, panthenol, hexylene glycol, propylene glycol, dipropylene glycol, sorbitol, derivatives thereof, and mixtures thereof.

Suspending Agents

The present topical cosmetic compositions may further comprise a suspending agent. Non-limiting examples of suitable suspending agents useful in the present compositions include one or more of alginic acid, bentonite, carbomer, carboxymethylcellulose and salts thereof, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and mixtures thereof.

Surfactants

The topical cosmetic compositions may optionally further comprise one or more surfactants. Suitable surfactants that can optionally be included in these compositions can comprise or consist of one or more of zwitterionic, amphoteric, anionic, cationic, and nonionic surfactants, and mixtures thereof. Suitable zwitterionic, amphoteric, anionic, cationic, and nonionic surfactants include those disclosed in McCutcheon's, *Detergents and Emulsifiers*, North American edition (1986), published by Allured Publishing Corporation, and McCutcheon's, *Functional Materials*, North American Edition (1992), both of which are hereby incorporated by reference herein in their entirety.

Non-limiting examples of surfactants useful in the present compositions include nonionic surfactants, anionic surfactants, amphoteric surfactants, cationic surfactants, and mixtures thereof.

Non-limiting examples of amphoteric surfactants useful in the present compositions are those selected from the group consisting of alkyl betaines, alkylamidobetaines, aminopropionates, iminodipropionates, aminoglycinates, imidazolinium betaines, sulfobetaines, and mixtures thereof.

Specific, non-limiting examples of amphoteric surfactants useful in the present compositions are those selected from the group consisting of sodium 3-dodecyl-aminopropionate, sodium 3-dodecylaminopropane sulfonate, sodium lauroamphoacetate, coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and mixtures thereof.

Similarly, non-limiting examples of anionic surfactants useful in the present compositions are those selected from the group consisting of alkyl sulfates, alkyl ethoxylated sulfates, beta-alkyloxy alkane sulfonates, alkyl ether sulfates, alkyl glyceryl ether sulfonates, alkyl ether carboxylates, acyl isethionates, acyl sarcosinates, acyl taurines, succinates, alkali metal, ammonium, or alkanolammonium salts thereof, and mixtures thereof.

Specific, non-limiting examples of anionic surfactants useful in the present compositions are those selected from the group consisting of ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, dioctyl esters of sodium sulfosuccinic acid, docusate sodium, and mixtures thereof.

Specific, non-limiting examples of cationic surfactants useful in the present compositions include those selected from the group consisting of behenyl trimethyl ammonium chloride, bis(acyloxyethyl) hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowdimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquaternium, stearalkonium chloride, stearyl dimethylbenzyl ammonium chloride, stearyl trimethyl ammonium chloride, trimethylglycine, and mixtures thereof.

Specific, non-limiting examples of nonionic surfactants useful in the present compositions include those selected from the group consisting of polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethyelen oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and mixtures thereof.

Vitamins

The present topical cosmetic compositions may optionally further comprise one or more vitamins or derivatives thereof. In an embodiment, the present topical cosmetic compositions in accordance with the subject matter described herein can comprise vitamin C and/or vitamin E. For example, vitamin C and/or vitamin E can be present in an amount effective to function as an antioxidant, either alone or in combination with other antioxidants, in the present topical cosmetic composition.

Penetration Enhancers

The present topical cosmetic compositions may optionally further comprise one or more penetration enhancers. Non-limiting examples of suitable penetration enhancers can include penetration enhancers that comprise or consist of one or more of a hydrophilic solvent, for example, DMSO, DMF, DMA, glycerol, polyethylene glycol, pyrrolidone derivatives, N-Decyl-methylsulfoxide (Brij 36T), lower alcohol's, fatty acids, and/or esters; a lipophilic enhancer, for example, dedecylazacycloheptane-2-one (azone), ethyl acetate, ethylpropionate, liquid paraffin, lamonin, lard, hexadecyl alcohol, oleyl alcohol, hydro ethyl lactamide, solketal, glycofural, tetrahydro-furfuryl alcohol, oleic acid, isopropyl myristate, lauryl alcohol, miglyol-oil, linoleic acid, lauric acid, dodecyl-L-pyroglutomate, and methyl laurate; a surfactant, for example an anionic surfactant, including for example, sodium lauryl sulfate, sodium dioctyl-sulfosuccinate, sorbitan monopalmitate, poloxamers, polyoxy-8-stearate, polyxyethelene-o-oleyl-ether, long chain alkyl sulfoxide, lauryl ether, Brij 36T, cetyl trimethyl ammonium bromide, and sodium oleate; a sunscreen, including for example, octyl methoxycinnamate, oxybenzone, homosalate, octyl salicylate, padimate-o, and sulisobenzone; a polymer; urea or a derivative thereof; liposomes; and/or combinations thereof.

Fragrances

The present topical cosmetic compositions may optionally further comprise a fragrance. Suitable non-limiting examples of fragrances can include essential oils and blends, for example, Perfume FAV22000 (BOUQUET® available from Firmenich), and any perfume.

Coloring Agents

The present topical cosmetic compositions may optionally further comprise a coloring agent, including but not limited to, one or more of a dye, a colorant, a pigment, a nanopigment, and/or combinations thereof.

Pigments can be present in the composition in an amount ranging from 0.01 to 25 wt. % of the final composition, for example, from 3 to 10 wt. %. They can be white or colored, inorganic or organic. Non-limiting examples include the titanium, zirconium or cerium oxides, as well as the zinc, iron or chromium oxides, ferric blue, chromium hydroxide, carbon black, ultramarines (polysulphides of aluminosilicates), manganese pyrophosphate and certain metal powders such as those of silver or of aluminium. Further non-limiting examples include the D&C pigments and the lakes commonly employed for imparting a make-up effect to the lips and to the skin, which include salts of calcium, of barium, of aluminium, of strontium or of zirconium.

Among the fat-soluble or water-soluble dyes that can be present in the composition, alone or as a mixture, in an amount ranging from 0.001 to 15 wt. %, for example from 0.01 to 5 wt. % or from 0.1 to 2 wt. %, relative to the total weight of the composition. Non-limiting examples include the disodium salt of ponceau, the disodium salt of alizarin green, quinoline yellow, amaranth trisodium salt, tartrazine disodium salt, rhodamine monosodium salt, fuchsin disodium salt, xanthophyll, methylene blue, carmine, halo-acid, azo and anthraquinone dyes, copper or iron sulphate, Sudan brown, Sudan red and annatto, as well as beetroot juice and carotene, and/or combinations thereof.

Other Embodiments

In an embodiment, the described topical cosmetic compositions can optionally further comprise at least one cosmetically acceptable excipient that can comprise or consist of at least one of an antioxidant that can comprise or consist of one or more members selected from the group consisting of butylated hydroxytoluene, sodium metabissulfite, butylated hydroxyl anisol, ascorbic acid and derivatives thereof, a sulfite and derivatives thereof, an ester, tocoferyl acetate, and combinations thereof; a chelating agent that can comprise or consist of one or more members selected from the group consisting of disodium edetate, EDTA, disodium EDTA, trisodium EDTA, tetrasodium EDTA, and combinations thereof; an emollient that can comprise or consist of one or more members selected from the group consisting of a glycol, a silicon-containing emollient, and combinations thereof; a thickening agent that can comprise or consist of one or more members selected from the group consisting of an acrylate copolymer, an acrylate, an acrylamide, a polysorbate, a fatty alcohol, a gum, a silicate, a carbomer derivative, a cellulose derivative, and combinations thereof; a preservative that can comprise or consist of one or more members selected from the group consisting of phenoxyethanol, methylisothiazolinone, phenoxyethanol, a paraben, imidazolynidyl urea, and combinations thereof; a pH adjuster that can comprise or consist of one or more members selected from the group consisting of triethanolamine, aminomethylpropanol, sodium hydroxide, and combinations thereof; and an emulsifier that can comprise or consist of one or more members selected from the group consisting of a $C_{14-22}$ alcohol, a $C_{12-20}$ alkylglucoside, and combinations thereof.

In a further embodiment, the present subject matter relates to a topical cosmetic composition wherein the emollient can comprise or consist of one or more members selected from the group consisting of propylene glycol, glycerin, butyleneglycol, pentyleneglycol, cyclopentasiloxane dimethicone crosspolymer, cyclopentasiloxane PEG/PPG-18/18 dimethicone, and combinations thereof, and/or the thickening agent can comprise or consist of one or more members selected from the group consisting of hydroxyethyl acrylate, sodium acryloyldimethyltaurate copolymer, squalane, polysorbate 60, a carbomer derivative, xanthan gum, carrageenan gum, aluminium silicate, magnesium silicate, a cellulose derivate, cetyl alcohol, stearyl alcohol, cetyl and stearyl alcohol, glyceryl stearate, and combinations thereof.

Topical Formulations

In an embodiment, the present topical cosmetic compositions are formulated in a serum, a gel cream, a lotion, a cream, an ointment, a gel, an aerosol, a foam, a foamable liquid, a solution (solubilized system), a paste, a suspension, a dispersion, an emulsion, a skin cleanser, a milk, a mask, a solid stick, a bar (such as a soap bar), an encapsulated formulation, a microencapsulated formulation, microspheres or nanospheres or vesicular dispersions, or other cosmetically acceptable topical dosage form. In the case of vesicular dispersions, the lipids of which the vesicles are made can be of the ionic or nonionic type, or a mixture thereof. The formulation can comprise one or more of an aqueous formulation and/or an anhydrous formulation.

In another embodiment, the present topical cosmetic composition in accordance with the subject matter described herein can comprise or consist of an anhydrous formulation, an aqueous formulation, or an emulsion.

In yet another embodiment, the present topical cosmetic compositions in accordance with the subject matter described herein are formulated in a serum or a gel cream.

Optional Additional Active Agents

The presently described topical cosmetic compositions can optionally further comprise one or more cosmetic active agents or dermatological active agents in addition to the described skin-lightening active agents. Such agents can include, for example, additional skin lightening active agents including plant derived and non-plant derived skin lightening agents, including for example, pigmentation inhibitors, tyrosinase inhibitors, and/or melanocyte melanogenesis inhibitors; and/or non-skin lightening active agents, including for example, optical brightening agents, sunscreen agents, anti-inflammatory agents, anti-microbial agents, anti-fungal agents, anti-wrinkle agents, anti-atrophy agents, anti-acne agents, free-radical scavengers, keratolytic agents, vitamins, anti-elastase and/or anti-collagenase agents, peptides, fatty acid derivatives, steroids, trace elements, extracts of algae and/or of planktons, enzymes and/or coenzymes, flavonoids and/or ceramides, a-hydroxy acids, and combinations thereof.

Additional Skin Lightening Active Agents

The topical cosmetic compositions may optionally further contain one or more additional skin lightening agents. Suitable additional skin lightening agents can comprise or consist of, but are not limited to, one or more of gingko extract, carob extract, rose fruit extract, geranium herb extract, *Perilla* extract, cinnamon extract, sweet marjoram extract, *Arnica* extract, Concha Blanca extract, cola ed Caballo, *Piri-Piri*, Pinon Negro, Pinon Blanco, extracts of clove, alfalfa, *Baliospermum montanum, Melia azadirachta, Convolvulus arvensis*, Gaiyo, Sansonin, Syuroyo, Seimkko, Soukyo, Taiso, Hakusempi, *Woodfordia fructosa, Lagerstroemia speciosa*, passiflorine, tepezcohite, amoule, Hobiyu, *Baffalo uri*, Achote, Guayule, Adhatoda, *Cymbopogon nardus, Desmodium gangeticum, Murraya koenigii, Smilax zeylanica, Gastrodia elata*, Karukeija, *Biota orientalis*, Kichiascoporia, Arecatachu, *Phyllostachys nigra* leaves, *Atractylodes japonica*, Koidzumi, *Tila, Camotede azafran, Jamaica, Poleo verde, Navo negro, Cyperus*, Kanzo, *Broussonetia*, Karojitsu, *Trichosanthis radix, Dioscorea phizoma*, and Aquilliaria.

Yet other skin lightening agents can comprise or consist of, but are not limited to, one or more of teprenone, dihydroxyisoquinoline, indomethacin, 3-hydroxymanule, vitamin K (such as vitamin K1-K7, its homologues, salts, and derivatives), thiazolidinone derivatives, and kynurenine and its derivatives and salts, retinol and its derivatives (e.g., Tretinoin, retinoic acid), resorcinol and its derivatives (e.g., 4-alkyl resorcinols, etc.), reservatol, *placenta* extracts, ellagic acid, linoleic acid and a-lipoic acid, and aminophenols e.g., such as those described in U.S. Pat. No. 6,203,781 (formula I). Amounts of additional skin lightening agents generally range from about 0.01% to about 20%, based on total weight of the composition. A suitable additional skin lightening agent is a-lipoic acid.

The cosmetic composition according to the present subject matter may optionally comprise a pigmentation inhibitor. Specific examples of the pigmentation inhibitor include, but are not limited to, p-aminobenzoic acid derivatives, salicylic acid derivatives, benzenesulfonamide derivatives, imidazole derivatives, naphthalene derivatives, hydroxyanthranilic acid or salts thereof and their derivatives, anthranilic acid derivatives, coumarin derivatives, amino acid derivatives (e.g., 2-amino-3-[1-carboxyl-2-(1H-imidazol-4-yl)ethyl]aminobutanoic acid, 2-amino-3-[1-carboxyl-2-(1H-imidazol-)ethyl]aminobutanoic acid hydrochloride, 2-amino-3-[1-carboxyl-2- (1H-imidazol-)ethyl]aminobutanoic acid sodium salt, and 2-amino-3-[1-carboxyl-2-(1H-imidazol-)ethyl]aminobutanoic acid potassium salt), benzotriazole derivatives, tetrazole derivatives, imidazoline derivatives, pyrimidine derivatives, dioxane derivatives, camphor derivatives, furan derivatives, pyrone derivatives, nucleic acid derivatives, allantoin derivatives, nicotinic acid derivatives, ascorbic acid or salts thereof and their derivatives (e.g., magnesium-L-ascorbic acid phosphate, ascorbyl palmitate, ascorbyl dipalmitate, ascorbic acid hydroxyproline phosphate ester, 5-o-alpha-D-glucopyranosyl-L-ascorbic acid, L-ascorbic acid phosphate ester sodium salt, L-ascorbic acid phosphate ester potassium salt, L-ascorbic acid phosphate ester magnesium salt, L-ascorbic acid phosphate ester calcium salt, L-ascorbic acid phosphate ester aluminum salt, L-ascorbic acid sulfate ester sodium salt, L-ascorbic acid sulfate ester potassium salt, L-ascorbic acid sulfate ester magnesium salt, L-ascorbic acid sulfate ester calcium salt, L-ascorbic acid sulfate ester aluminum salt, L-ascorbic acid sodium salt, L-ascorbic acid potassium salt, L-ascorbic acid magnesium salt, L-ascorbic acid calcium salt, L-ascorbic acid aluminum salt, 6-o-alpha-D-galactopyranosyl-L-ascorbic acid, 2-o-beta-D-galactopyranosyl-L-ascorbic acid, L-ascorbic acid phosphate ester magnesium salt, L-ascorbic acid phosphate ester sodium salt, L-ascorbic acid sulfate ester sodium salt, 6-o-acylascorbic acid phosphate ester sodium salt, 6-o-acylascorbic acid phosphate ester ammonium salt, 6-o-acylascorbic acid phosphate ester isopropanolamine salt, 3-o-isopropyl-L-ascorbic acid, 6-o-alkylascorbic acid phosphate ester potassium salt, 6-o-alkylascorbic acid phosphate ester calcium salt, 6-o-alkylascorbic acid phosphate ester barium salt, 6-o-alkylascorbic acid phosphate ester ammonium salt, 6-o-alkylascorbic acid phosphate ester monoethanolamine salt, 6-o-alkylascorbic acid phosphate ester diethanolamine salt, 6-o-alkylascorbic acid phosphate ester triethanolamine salt, 6-o-alkylascorbic acid phosphate ester monoisopropanolamine salt, 6-o-alkylascorbic acid phosphate ester diisopropanolamine salt, 6-o-alkylascorbic acid phosphate ester triisopropanolamine salt, 3-o-glycosy-L-ascorbic acid, 6-o-beta-D-galactopyranosyl-L-ascorbic acid, ascorbic acid cholesterol phosphate ester, L-ascorbyl palmitate, L-ascorbyl isopalmitate, L-ascorbyl dipalmitate, L-ascorbyl diisopalmitate, L-ascorbyl stearate, L-ascorbyl isostearate, L-ascorbyl distearate, L-ascorbyl diisostearate, L-ascorbyl myristate, L-ascorbyl isomyristate, L-ascorbyl dimyristate, L-ascorbyl diisomyristate, L-ascorbyl 2-ethylhexanoate, L-ascorbyl di-2-ethylhexanoate, oleic acid-L-ascorbic acid, 2-o-alpha-D-glucosyl-L-ascorbic acid, 2-o-alpha-D-maltosyl-L-ascorbic acid, 2-o-alpha-D-maltotriosyl-L-ascorbic acid, 3-o-alpha-D-glucosyl-L-ascorbic acid, 2-o-alpha-D-maltosyl-L-ascorbic acid, 2-o-alpha-D-maltotriosyl-L-ascorbic acid, L-ascorbic acid tetraisopalmitate ester, L-ascorbic acid tetralaurate ester, L-ascorbic acid tetra-2-ethylhexanoate ester, L-ascorbic acid tetraoleate ester, 5,6-isopropylidene-L-ascorbic acid, L-ascorbic acid retinol ester, L-ascorbic acid-DL-tocopherol phosphate ester, L-3-o-ethylascorbic acid, L-ascorbic acid tristearate, L-ascorbic acid tripalmitate, L-ascorbic acid trioleate, ascorbic acid triphosphate ester, 2-o-ascorbyl cinnamate, 2-o-ascorbyl ferulate, 2-o-ascorbyl caffeate, 2-o-ascorbyl sinapate, 2-o-[6-palmitoylascorbyl]-4'-acetoxy ferulate, DL-alpha-tocopherol-2-L-ascorbic acid phosphate diester, ascorbic acid inositol-binding derivatives, ascorbic acid phosphorus amide derivatives, ascorbic acid-arbutin binding compounds, ascorbyl-phosphoryl-cholesterol, chromanyl ascorbic acid derivatives, and ascorbic acid/sialic acid derivatives), tocopherol or salts thereof and their derivatives (e.g., alpha-tocopherol, beta-tocopherol, gamma-tocopherol, delta-tocopherol, epsilon-tocopherol, alpha-tocopheryl retinoate, aminomethylated tocopherol, hydroxymethylated tocopherol, tocopheryl phosphate ester, tocopherol acetate, tocopherol nicotinate, tocopherol succinate, tocopherol linoleate, tocopherol orotate, DL-alpha-tocopheryl glucoside, DL-alpha-tocopherylmaltoside, DL-beta-tocopheryl glucoside, DL-beta-tocopherylmaltoside, DL-gamma-tocopheryl glucoside, DL-gamma-tocopherylmaltoside, DL-delta-tocopheryl glucoside, DL-delta-tocopherylmaltoside, D-alpha-tocopheryl glucoside, D-alpha-tocopherylmaltoside, D-beta-tocopheryl glucoside, D-beta-tocopherylmaltoside, D-gamma-tocopheryl glucoside, D-gamma-tocopherylmaltoside, D-delta-tocopheryl glucoside, D-delta-tocopherylmaltoside, L-alpha-tocopheryl glucoside, L-alpha-tocopherylmaltoside, L-beta-tocopheryl glucoside, L-beta-tocopherylmaltoside, L-gamma-tocopheryl glucoside, L-gamma-tocopherylmaltoside, L-delta-tocopheryl glucoside, L-delta-tocopherylmaltoside, 1-(sulfoethylamino)-3-(alpha-tocopheryl-6-yloxy)propan-2-ol, 1-(carboxypropylamino)-3-(alpha-tocopheryl-6-yloxy)propan-2-ol hydrochloride, S-[3-(alpha-tocopheryl-6-yloxy)-2-hydroxypropyl]cysteine, S-[3-(alpha-tocopheryl-6-yloxy)-2-hydroxypropyl]-gamma-glutamyl cysteinyl glycine, N-[3-(alpha-tocopheryl-6-yloxy)-2-hydroxypropyl]aspartic acid, and N-[3-(alpha-tocopheryl-6-yloxy)-2-hydroxypropyl] glutamic acid), tocotrienol or salts thereof and their derivatives (e.g., alpha-tocotrienol, beta-tocotrienol, gamma-tocotrienol, delta-tocotrienol, tocotrienol acetate, tocotrienol nicotinate, tocotrienol succinate, tocotrienol linoleate, and tocotrienol orotate), kojic acid or derivatives thereof (e.g., 2-methoxymethyl-hydroxy-4H-pyran-, 2-ethoxymethyl-5-hydroxy-4H-pyran-, 2-benzoyloxymethyl-5-hydroxy-4H-pyran-, 2-cinnamoyloxymethyl-5-hydroxy-4H-pyran-, 2-phenoxymethyl-5-hydroxy-4H- pyran-, kojic acid glycoside, geranyl acetone, kojic acid monobutylate, kojic acid monocaprate, kojic acid monopalmitate, kojic acid monostearate, kojic acid monocinnamate, kojic acid monobenzoate, kojic acid dibutyrate, kojic acid dipalmitate, kojic acid distearate, and kojic acid dioleate), oxybenzone, benzophenone, guaiazulene, shikonin, baicalin or salts thereof and their derivatives, baicalein or salts thereof and their derivatives, berberine or salts thereof and their derivatives, chrysin or salts thereof and their derivatives, apigenin or salts thereof and their derivatives, luteolin or salts thereof and their derivatives, acacetin or salts thereof and their derivatives, diosmetin or salts thereof and their derivatives, kaempferol or salts thereof and their derivatives, triforine or salts thereof and their derivatives, astragalin or salts thereof and their derivatives, quercetin or salts thereof and their derivatives, quercitrin or salts thereof and their derivatives, isoquercitrin or salts thereof and their derivatives, rutin or salts thereof and their derivatives, morin or salts thereof and their derivatives, myricetin or salts thereof and their derivatives, myricitrin or salts thereof and their derivatives, datiscetin or salts thereof and their derivatives, quercetagetin or salts thereof and their derivatives, isorhamnetin or salts thereof and their derivatives, pinocembrin or salts thereof and their derivatives, naringenin or salts thereof and their derivatives, hesperetin or salts thereof and their derivatives, eriodictyol or salts thereof and their derivatives, pinobanksin or salts thereof and their derivatives, aromadendrin or salts thereof and their derivatives, engeletin or salts thereof and their derivatives, taxifolin or salts thereof and their derivatives, astilbin or salts thereof and their derivatives, ampelopsin or salts thereof and their derivatives, spiraeoside, kaempferol-7-neohesperidoside, glutathione or salts thereof and their derivatives, isoflavone glycosides (e.g., 6-o-apiosylpuerarin-4'-o-glucoside, 6-o-glucosylpuerarin, 3'-hydroxypuerarin-4'-o-glucoside, and 6-o-apiosyl-3'-hydroxypuerarin), gamma-pyrone glycosides (e.g., maltol-3-o-(6'-o-apiosyl)-glucoside, and maltol-3-o-(6'-o-apiosyl)-glucoside), isononyl ferulate, ellagic acid or salts thereof and their derivatives (e.g., 5,4-dimethylellagic acid, 3,3'-dimethylellagic acid, 3,3',4-trimethylellagic acid, 3,3',4,4'-tetramethyl-5-methoxyellagic acid, 3-ethyl-4-methyl-5-hydroxyellagic acid, and amritoside), lucinol, onjisaponin, Ophiopogonis saponin, ruscogenin, sericoside, asiaticoside, hederin, senegin, benzoic acid anilides (e.g., 4-hydroxy-N-(2-hydroxyphenyl)benzoic acid amide, 4-hydroxy-N-(3-hydroxyphenyl)benzamide, 4-hydroxy-N-(4-hydroxyphenyl)benzamide, 3,5-di-t-butyl-4-hydroxy-N-(4-hydroxyphenyl)benzamide, 3,5-di-t-butyl-4-hydroxy-N-(3-hydroxyphenyl)benzamide, and 3,5-di-t-butyl-4-hydroxy-N-(2-hydroxyphenyl)benzamide), diphenylpyraline, ciproheptadine, triprolidine, dimethindene, ozagrel, isothipendyl, iproheptine, homochlorcyclizine, alimemazine, bucillamine, okitosamide, vidarabine, xanthotoxol, phenylmercuric hexachlorophene, mercuric oxide, mercurous chloride, aqueous hydrogen peroxide, zinc peroxide, *placenta* extracts (e.g., those derived from bovine *placenta*, swine *placenta*, equine *placenta*, and ovine *placenta*), almond (BIAN TAO) extract, *Foeniculum vulgare* leaf extract, *Atractylodes ovata* extract, *Atractylodes japonica* extract, konfuyou extract, *Uncaria* extract, *Uncaria gambir* extract, kakoujyuyou extract, *Glycyrrhizae radix* extract, *Gardenia jasminoides* (ZHI ZI) extract, kuranigean extract, *Sophora flavescens* extract, Scutellaria *baicalensis* (HUANG QIN) extract, *Triticum aestivum* L. (wheat) extract, *Oryza sativa* L. (rice) extract, *Coriaria* extract, *Woodfordia fruticosa* Sidowayah extract, sanukyu extract, sanbitoro extract, *Cassia* Mimosoides L. extract, *Bletilla striata* (BAIJI) extract, *Ligusticum chuanxiong* (CHUAN XIONG) extract, *Cassia acutifolia* extract, *Inula britannica* extract, *Lythrum anceps* extract, surigatin extract, *Angelica decursiva* (QIAN HU) extract, *Coix lachryma-jobi* L. (YI YI REN) extract, *Vitex rotundifolia* L. extract, *Vitex trifolia* (MAN JING ZI) extract, *Hamamelis virginiana* extract, palm extract, *Parietaria* extract, *Carthamus tinctorius* (HONG HUA) extract, *Morus alba* L. (SANG BAI PI) extract, *Sophora flavescens* (KU SHEN) extract, *Iris germanica* L. extract, *Iris florentina* L. extract, *Artemisia mongolia* extract, *Alnus firma* fruit extract, Hong Kong extract, *Sanguisorba officinalis* (DI YU) extract, *Daphniphyllum macropodum* extract, *Polygonum multiflorum* extract, and *Fatsia japonica* extract.

The cosmetic composition according to the present subject matter may contain a tyrosinase inhibitor. Specific examples of the tyrosinase inhibitor include ascorbic acid or salts thereof and their derivatives (e.g., magnesium-L-ascorbic acid phosphate, ascorbyl palmitate, ascorbyl dipalmitate, ascorbic acid hydroxyproline phosphate ester, 5-o-alpha-D-glucopyranosyl-L-ascorbic acid, L-ascorbic acid phosphate ester sodium salt, L-ascorbic acid phosphate ester potassium salt, L-ascorbic acid phosphate ester magnesium salt, L-ascorbic acid phosphate ester calcium salt, L-ascorbic acid phosphate ester aluminum salt, L-ascorbic acid sulfate ester sodium salt, L-ascorbic acid sulfate ester potassium salt, L-ascorbic acid sulfate ester magnesium salt, L-ascorbic acid sulfate ester calcium salt, L-ascorbic acid sulfate ester aluminum salt, L-ascorbic acid sodium salt, L-ascorbic acid potassium salt, L-ascorbic acid magnesium salt, L-ascorbic acid calcium salt, L-ascorbic acid aluminum salt, 6-o-alpha-D-galactopyranosyl-L-ascorbic acid, 2-o-beta-D-galactopyranosyl-L-ascorbic acid, L-ascorbic acid phosphate ester magnesium salt, L-ascorbic acid phosphate ester sodium salt, L-ascorbic acid sulfate ester sodium salt, 6-o-acylascorbic acid phosphate ester sodium salt, 6-o-acylascorbic acid phosphate ester ammonium salt, 6-o-acylascorbic acid phosphate ester isopropanolamine salt, 3-o-isopropyl-L-ascorbic acid, 6-o-alkylascorbic acid phosphate ester potassium salt, 6-o-alkylascorbic acid phosphate ester calcium salt, 6-o-alkylascorbic acid phosphate ester barium salt, 6-o-alkylascorbic acid phosphate ester ammonium salt, 6-o-alkylascorbic acid phosphate ester monoethanolamine salt, 6-o-alkylascorbic acid phosphate ester diethanolamine salt, 6-o-alkylascorbic acid phosphate ester triethanolamine salt, 6-o-alkylascorbic acid phosphate ester monoisopropanolamine salt, 6-o-alkylascorbic acid phosphate ester diisopropanolamine salt, 6-o-alkylascorbic acid phosphate ester triisopropanolamine salt, 3-o-glycosy-L-ascorbic acid, 6-o-beta-D-galactopyranosyl-L-ascorbic acid, ascorbic acid cholesterol phosphate ester, L-ascorbyl palmitate, L-ascorbyl isopalmitate, L-ascorbyl dipalmitate, L-ascorbyl diisopalmitate, L-ascorbyl stearate, L-ascorbyl isostearate, L-ascorbyl distearate, L-ascorbyl diisostearate, L-ascorbyl myristate, L-ascorbyl isomyristate, L-ascorbyl dimyristate, L-ascorbyl diisomyristate, L-ascorbyl 2-ethylhexanoate, L-ascorbyl di-2-ethylhexanoate, oleic acid-L-ascorbic acid, 2-o-alpha-D-glucosyl-L-ascorbic acid, 2-o-alpha-D-maltosyl-L-ascorbic acid, 2-o-alpha-D-maltotriosyl-L-ascorbic acid, 3-o-alpha-D-glucosyl-L-ascorbic acid, 2-o-alpha-D-maltosyl-L-ascorbic acid, 2-o-alpha-D-maltotriosyl-L-ascorbic acid, L-ascorbic acid tetraisopalmitate ester, L-ascorbic acid tetralaurate ester, L-ascorbic acid tetra-2-ethylhexanoate ester, L-ascorbic acid tetraoleate ester, 5,6-isopropylidene-L-ascorbic acid, L-ascorbic acid retinol ester, L-ascorbic acid-DL-tocopherol phosphate ester, L-3-o-ethylascorbic acid, L-ascorbic acid tristearate, L-ascorbic acid tripalmitate, L-ascorbic acid trioleate, ascorbic acid triphosphate ester, 2-o-ascorbyl cinnamate, 2-o-ascorbyl ferulate, 2-o-ascorbyl caffeate, 2-o-ascorbyl sinapate, 2-o-[6-palmitoylascorbyl]-4'-acetoxy ferulate, DL-alpha-tocopherol-2-L-ascorbic acid phosphate diester, ascorbic acid inositol-binding derivatives, ascorbic acid phosphorus amide derivatives, ascorbic acid-arbutin binding compounds, ascorbyl-phosphoryl-cholesterol, chromanyl ascorbic acid derivatives, and ascorbic acid/sialic acid derivatives), kojic acid or salts thereof and their derivatives (e.g., 2-methoxymethyl-hydroxy-4H-pyran-, 2-ethoxymethyl-5-hydroxy-4H-pyran-, 2-benzoyloxymethyl-5-hydroxy-4H-pyran-, 2-cinnamoyloxymethyl-5-hydroxy-4H-pyran-, 2-phenoxymethyl-5-hydroxy-4H-pyran-, kojic acid glycoside, geranyl acetone, kojic acid monobutylate, kojic acid monocaprate, kojic acid monopalmitate, kojic acid monostearate, kojic acid monocinnamate, kojic acid monobenzoate, kojic acid dibutyrate, kojic acid dipalmitate, kojic acid distearate, and kojic acid dioleate), tocopherol or salts thereof and their derivatives (e.g., alpha-tocopherol, beta-tocopherol, gamma-tocopherol, delta-tocopherol, epsilon-tocopherol, alpha-tocopheryl retinoate, aminomethylated tocopherol, hydroxymethylated tocopherol, tocopheryl phosphate ester, tocopherol acetate, tocopherol nicotinate, tocopherol succinate, tocopherol linoleate, tocopherol orotate, DL-alpha-tocopheryl glucoside, DL-alpha-tocopherylmaltoside, DL-beta-tocopheryl glucoside, DL-beta-tocopherylmaltoside, DL-gamma-tocopheryl glucoside, DL-gamma-tocopherylmaltoside, DL-delta-tocopheryl glucoside, DL-delta-tocopherylmaltoside, D-alpha-tocopheryl glucoside, D-alpha-tocopherylmaltoside, D-beta-tocopheryl glucoside, D-beta-tocopherylmaltoside, D-gamma-tocopheryl glucoside, D-gamma-tocopherylmaltoside, D-delta-tocopheryl glucoside, D-delta-tocopherylmaltoside, L-alpha-tocopheryl glucoside, L-alpha-tocopherylmaltoside, L-beta-tocopheryl glucoside, L-beta-tocopherylmaltoside, L-gamma-tocopheryl glucoside, L-gamma-tocopherylmaltoside, L-delta-tocopheryl glucoside, L-delta-tocopherylmaltoside, L-(sulfoethylamino)-3-(alpha-tocopheryl-6-yloxy)propan-2-ol, 1-(carboxypropylamino)-3-(alpha-tocopheryl-6-yloxy)propan-2-ol hydrochloride, S-[3-(alpha-tocopheryl-6-yloxy)-2-hydroxypropyl]cysteine, S-[3-(alpha-tocopheryl- 6-yloxy)-2-hydroxypropyl]-gamma-glutamyl cysteinyl glycine, N-[3-(alpha-tocopheryl-6-yloxy)-2-hydroxypropyl] aspartic acid, and N-[3-(alpha-tocopheryl-6-yloxy)-2-hydroxypropyl]glutamic acid), tocotrienol or salts thereof and their derivatives (e.g., alpha-tocotrienol, beta-tocotrienol, gamma-tocotrienol, delta-tocotrienol, tocotrienol acetate, tocotrienol nicotinate, tocotrienol succinate, tocotrienol linoleate, and tocotrienol orotate), N-acetyl tyrosine or salts thereof and their derivatives, glutathione or salts thereof and their derivatives, ellagic acid or salts thereof and their derivatives (e.g., 3,4-dimethylellagic acid, 3,3'-dimethylellagic acid, 3,3',4-trimethylellagic acid, 3,3',4,4'-tetramethyl-5-methoxyellagic acid, 3-ethyl-4-methyl-5-hydroxyellagic acid, and amritoside), isonitrile antibiotics such as isonitrin A, isonitrin B, isonitrin C, isonitrin D, isonitrinic acid E, isonitrinic acid F, derumadein, and toricobilidein, orsellinic acid derivatives (e.g., orsellinic acid, orsellinic acid ethyl ester orcinol, p-geranyl orsellinic acid, p-geranyl orsellinic acid ethyl ester geranyl orcinol, p-farnesyl orsellinic acid, p-farnesyl orsellinic acid ethyl ester farnesyl orcinol, p-dodecanyl orsellinic acid, p-dodecanyl orsellinic acid ethyl ester dodecanyl orcinol, p-tetradecanyl orsellinic acid, p-tetradecanyl orsellinic acid ethyl ester tetradecanyl orcinol, p-hexadecanyl orsellinic acid, p-hexadecanyl orsellinic acid ethyl ester hexadecanyl orcinol, p-undecanyl orsellinic acid, p-undecanyl orsellinic acid ethyl ester undecanyl orcinol, p-tridecanyl orsellinic acid, p-tridecanyl orsellinic acid ethyl ester undecanyl orcinol, p-pentadecanyl orsellinic acid, p-pentadecanyl orsellinic acid ethyl ester pentadecanyl orcinol, ethylhexyl orsellinic acid, p-ethylhexyl orsellinic acid ethyl ester ethylhexyl orcinol, p-cyclohexylmethyl orsellinic acid, p-cyclohexylmethyl orsellinic acid ethyl ester cyclohexylmethyl orcinol, p-hydroxyethylhexyl orsellinic acid methyl ester, and p-hydroxyethylhexyl orsellinic acidhydroxyethylhexyl orcinol), umbellic acid, brefeldin, oxydesberatrol, resorcinol derivatives (4-cyclohexyl resorcinol), 3-hydroxyketone compounds (e.g., 1,5-bis(p-hydroxyphenyl)-2-hydroxypentan-4-one, 1,5-bis(o,p-dihydroxyphenyl)-2-hydroxypentan-4-one, and 1,5-bis(p-hydroxyphenyl-m-methoxyphenyl)-2-hydroxypentan-4-one), 1,3-diketone compounds (e.g., 1,5-bis (p-hydroxyphenyl)-2,4-pentanedione, 1,5-bis(o,p-dihydroxyphenyl)-2,4-pentanedione, and 1,5-bis(p-hydroxyphenyl-m-methoxyphenyl)-2,4-pentanedione), bishydroxybenzylamides, gamma-aminobutyric acid or derivatives thereof (e.g., N-methyl-gamma-aminobutyric acid, N-dimethyl-gamma-aminobutyric acid, and gamma-aminobutyric acid oleyl ester), hydrogen peroxide, zinc peroxide, *placenta* extracts, lucinol, silk extract, *acacia* extract, acelora extract, *Abutilon theophrasti* (Semen Abutili) extract, *Betula pendula* extract, *quercus* (MO SHI ZI; chestnut gall wasp) extract, chestnut extract, *Plectranthus kameba* extract, *Isodon trichocarpus* extract, *Plectranthus japonicus* (dried) extract, *Oenanthe stolonifera* extract, *Fagopyrum esculentum* extract, *Durvillea* extract, *Capsella bursa-pastoris* extract, *Eupatorium japonicum* (dried) extract, *Matricaria chamomilla* L. extract, *Morus alba* extract, *Gardenia jasminoides* extract, *Angelica acutiloba* extract, *Sanguisorba officinalis* extract, *Sophora flavescens* extract, *Artemisia indica* extract, *Lonicera japonica* extract, *Phellodendron amurense* extract, *Houttuynia cordata* extract, *Poria cocos* extract, *Coix lachryma-jobi* L. extract, *Lamium album* var. *barbatum* extract, *Humulus lupulus* extract, *Crataegus cuneata* extract, *eucalyptus* extract, *Achillea millefolium* extract, althaea extract, GUI PI (*Cinnamomum cassia* bark; *Cinnamomi* Cortex) extract, MAN JING ZI (*Vitex rotundifolia* fruit) extract, *Hamamelis virginiana* extract, *Morus bombycis* extract, *Platycodon grandiflorum* extract, TU SI ZI (*Cuscuta chinensis* Lam. seed) extract, HSU SUI TZU (*Euphorbia lathyris* seed) extract, SHE GAN (*Belamcanda chinensis* rhizome) extract, MA HUANG (*Ephedra sinica* stem and leaf; Ephedrae Herba) extract, CHUAN XIONG (*Cnidium officinale* rhizome; Cnidii Rhizoma) extract, DU HUO (*Aralia cordata* root and rhizome) extract, CHAI HU (*Bupleurum falcatum* root; Bupleuri Radix) extract, FANG FENG (*Saposhnikovia divaricata* root; Saposhnikoviae Radix) extract, BEI SHA SHEN (*Glehnia littoralis* root; Glehniae Radix cum Rhizoma) extract, HUANG QIN (*Scutellaria baicalensis* root; Scutellariae Radix) extract, MU DAN PI (*Paeonia suffruticosa* root; Moutan Cortex) extract, SHAO YAO (*Paeonia lactifolia* root; Paeoniae Radix) extract, Geranium *thunbergii* extract, GE GEN (*Pueraria lobata* root; Puerariae Radix) extract, WU BEI ZI (Galla Rhois) extract, *Aloe arborescens* extract, SHENG MA (Cimicifuga simplex root; Cimicifugae Rhizoma) extract, HONG HUA (*Carthamus tinctorius* flower; *Carthami* Flos) extract, green tea extract, red tea extract, and *Acacia catechu* extract.

The cosmetic composition according to the present subject matter may contain a melanocyte melanogenesis inhibitor. Specific examples of the melanocyte melanogenesis inhibitor include lobeline or lobeline derivatives, liquiritin derivatives (e.g., liquiritin-alpha-glucoside, and liquiritin-alpha-maltoside), phenylchroman derivatives, chromone derivatives (e.g., 2-butylchromone, 2-pentylchromone, 2-heptylchromone, 2-nonylchromone, 2-hexadecylchromone, 2-(1-ethylpentyl)chromone, 2-butyl-7-methoxychromone, 2-pentyl-7-methoxychromone, 2-heptyl-7-methoxychromone, 2-nonyl-7-methoxychromone, 2-pentadecyl-7-methoxychromone, 2-(1-ethylpentyl)-7-methoxychromone, 7-hydroxy-2-methylchromone, 7-hydroxy-2-butylchromone, 7-hydroxy-2-pentylchromone, 7-hydroxy-2-heptylchromone, 7-hydroxy-2-nonylchromone, 7-hydroxy-2-pentadecylchromone, and 7-hydroxy-2-(1-ethylpentyl) chromone), azelaic acid derivatives (e.g., azelaic acid monoalkyl ester, and azelaic acid dialkyl ester), phosphatidylglucosamine, lysophosphatidylglucosamine, 3-beta-D-glucopyranosyl manool, 3-beta-D-maltopyranosyl manool, substituted amino acid derivatives (e.g., DL-N-formyl-3-(1-naphthyl)alanine, DL-N-acetyl-3-(1-naphthyl)alanine, DL-N-propionyl-3-(1-naphthyl)alanine, DL-N-butyryl-3-(1-naphthyl)alanine, DL-N-isobutyryl-3-(1-naphthyl)alanine, DL-N-valeryl-3-(1-naphthyl)alanine, DL-N-isovaleryl-3-(1-naphthyl)alanine, DL-N-(2-methylvaleryl)-3-(1-naphthyl) alanine, DL-N-(3-methylvaleryl)-3-(1-naphthyl)alanine, DL-N-(4-methylvaleryl)-3-(1-naphthyl)alanine, DL-N-t-butylacetyl-3-(1-naphthyl)alanine, DL-N-pivaloyl-3-(1-naphthyl)alanine, DL-N-caproyl-3-(1-naphthyl)alanine, DL-N-(2-ethylhexanoyl)-3-(1-naphthyl)alanine, DL-N-(2-methylhexanoyl)-3-(1-naphthyl)alanine, DL-N-heptanoyl-3-(1-naphthyl)alanine, DL-N-octanoyl-3-(1-naphthyl) alanine, DL-N-(2-propylpentanoyl)-3-(1-naphthyl)alanine, DL-N-nonanoyl-3-(1-naphthyl)alanine, DL-N-decanoyl-3-(1-naphthyl)alanine, DL-N-undecanoyl-3-(1-naphthyl)alanine, DL-N-dodecanoyl-3-(1-naphthyl)alanine, DL-N-tridecanoyl-3-(1-naphthyl)alanine, DL-N-tetradecanoyl-3-(1-naphthyl)alanine, DL-N-pentadecanoyl-3-(1-naphthyl) alanine, DL-N-hexadecanoyl-3-(1-naphthyl)alanine, DL-N-heptadecanoyl-3-(1-naphthyl)alanine, DL-N-octadecanoyl-3-(1-naphthyl)alanine, DL-N-nonadecanoyl-DL-3-(1-naphthyl)alanine, DL-N-icosanoyl-3-(1-naphthyl)alanine, DL-N-acroyl-3-(1-naphthyl)alanine, DL-N-crotonyloyl-3-(1-naphthyl)alanine, DL-N-methacryloyl-3-(1-naphthyl)alanine, DL-N-vinylacetyl-3-(1-naphthyl)alanine, DL-N-cyclopropanoyl-3-(1-naphthyl)alanine, DL-N-(2-pentenoyl)-3-(1-naphthyl)alanine, DL-N-(4-pentenoyl)-3-(1-naphthyl)

alanine, DL-N-(2-hexenoyl)-3-(1-naphthyl)alanine, DL-N-(3-hexenoyl)-3-(1-naphthyl)alanine, DL-N-(2-methyl-3-pentenoyl)-3-(1-naphthyl)alanine, DL-N-cyclohexenoyl-3-(1-naphthyl)alanine, DL-N-(10-undecenoyl)-3-(1-naphthyl)alanine, DL-N-linoleyl-3-(1-naphthyl)alanine, DL-N-hydroxyacetyl-3-(1-naphthyl)alanine, DL-N-(6-hydroxycaproyl)-3-(1-naphthyl)alanine, DL-N-(8-hydroxyoctanoyl)-3-(1-naphthyl)alanine, DL-N-(9-hydroxynonanoyl)-3-(1-naphthyl)alanine, DL-N-(10-hydroxydecanoyl)-3-(1-naphthyl)alanine, DL-N-(11-hydroxyundecanoyl)-3-(1-naphthyl)alanine, DL-N-(12-hydroxydecanoyl)-3-(1-naphthyl)alanine, DL-N-benzoyl-3-(1-naphthyl)alanine, DL-N-(2-hydroxybenzoyl)-3-(1-naphthyl)alanine, DL-N-(3-hydroxybenzoyl)-3-(1-naphthyl)alanine, DL-N-(4-hydroxybenzoyl)-3-(1-naphthyl)alanine, DL-N-(o-toluyl)-3-(1-naphthyl)alanine, DL-N-(m-toluyl)-3-(1-naphthyl)alanine, DL-N-(p-toluyl)-3-(1-naphthyl)alanine, DL-N-(1-naphthoyl)-3-(1-naphthyl)alanine, DL-N-(2-naphthoyl)-3-(1-naphthyl)alanine, DL-N-(2-carboxybenzoyl)-3-(1-naphthyl)alanine, DL-N-(3-carboxybenzoyl)-3-(1-naphthyl)alanine, DL-N-(4-carboxybenzoyl)-3-(1-naphthyl)alanine, DL-N-(2-picolyloyl)-3-(1-naphthyl)alanine, DL-N-(3-picolyloyl)-3-(1-naphthyl)alanine, DL-N-(4-picolyloyl)-3-(1-naphthyl)alanine, DL-N-phenylacetyl-3-(1-naphthyl)alanine, DL-N-(2-phenylpropanoyl)-3-(1-naphthyl)alanine, DL-N-(3-phenylbutyryl)-3-(1-naphthyl)alanine, DL-N-(4-methylvaleryl)-3-(1-naphthyl)alanine, DL-N-valeryl-3-(1-naphthyl)alanine, DL-N-(4-methylvaleryl)-3-(1-naphthyl)alanine amide, DL-N-(4-methylvaleryl)-3-(1-naphthyl)alanine methyl ester, DL-N-(4-methylvaleryl)-3-(1-naphthyl)alanine ethyl ester, DL-N-(4-methylvaleryl)-3-(1-naphthyl)alanine propyl ester, DL-N-(4-methylvaleryl)-3-(1-naphthyl)alanine-N-butyl ester, DL-N-(4-methylvaleryl)-3-(1-naphthyl)alanine pentyl ester, DL-N-(4-methylvaleryl)-3-(1-naphthyl)alanine isopropyl ester, DL-N-(4-methylvaleryl)-3-(1-naphthyl)alanine isobutyl ester, and DL-N-(4-methylvaleryl)-3-(1-naphthyl)alanine-t-butyl ester), benzolactam derivatives, indolactam derivatives, cedrol, guaiol, 1-(4-hydroxyphenylthio)-2-propanol, beta-lactoglobulin, 2-methoxy-5-methylphenol, 5-ethyl-2-methoxyphenol, 5-N-propyl-2-methoxyphenol, 5-N-butyl-2-methoxyphenol, 5-N-hexyl-2-methoxyphenol, 5-N-heptyl-2-methoxyphenol, 5-N-decyl-2-methoxyphenol, 5-(1,1-dimethylpropyl)-2-methoxyphenol, 5-(1,1-dimethylbutyl)-2-methoxyphenol, 5-(1,1-dimethylethyl)-2-methoxyphenol, 2-methoxy-5-(1-methylpentyl)phenol, 2-methoxy-5-(1-methylhexyl)phenol, 2-methoxy-5-(3-methylhexyl)phenol, 2-methoxy-5-(6-methylheptyl)phenol, 5-(1,3-dimethylheptyl)-2-methoxyphenol, mulberrin, ferruginol, sugiol, cryptojaponol, 1,5-bis[p-hydroxyphenyl]-1,4-pentadien-3-one, 1,5-bis[o-hydroxyphenyl]-1,4-pentadien-3-one, 1,5-bis[2,4-dihydroxyphenyl]-1,4-pentadien-3-one, 1,5-bis[3-methoxy-4-hydroxyphenyl]-1,4-pentadien-3-one, haginine, agrimophol, agrimol, hydrangenol or derivatives thereof, and alkylresorcinol or derivatives thereof (e.g., 4-N-butylresorcinol), aristolone, calamenenes (e.g., calamenene, 7-hydroxycalamenene, 5-hydroxycalamenene, and 7-methoxycalamenene), trans-umbellic acid, N-alpha-benzoyl-L-arginine, N-alpha-benzoyl-L-arginine ethyl ester or N-alpha-benzoyl-L-arginine ethyl ester, 5-methyl-2(3H)-furanone, 2-buten-4-olide, 2-hydroxymethylfuran, 2,5-dimethyl-4-hydroxy-3(2H)-furanone, 2-formylfuran, 3-formylfuran, methyl alpha-furyl ketone, furfuryl acetate, 2-hydroxy-3-methyl-2-cyclopenten-1-one, 2-hydroxy-3,5-dimethyl-2-cyclopenten-1-one, 2,5-dimethyl-4-hydroxy-3(2H)-thiophenone, 2-hydroxy-3-ethyl-2-cyclopenten-1-one, tetronic acid, pentanedione, iminodibenzyls (e.g., 2,2'-iminodibenzyl, imipramine, imipramine hydrochloride, desipramine, desipramine hydrochloride, chlorimipramine, and trimipramine), dibenzocycloheptadienes (e.g., amitriptyline, amitriptyline hydrochloride, nortriptyline, and noxiptyline), tetrahydrocopalol glycoside (e.g., ketotifen fumarate, labda-8(17),13-dien-15-ol, tetrahydromanool, tetrahydrocopalol, tetrahydrocopalol glucoside, tetrahydrocopalol galactoside, tetrahydrocopalol maltoside, tetrahydrocopalol cellobioside, and tetrahydrocopalol maltotrioside), spiro ether compounds, piochelin, phenothiazine compounds, promethazine, alimemazine, alimemazine tartrate, triflupromazine, levomepromazine, chlorpromazine, cyclandelate, 4-carboxymethyloxybenzoic acid, 4-carboxymethyloxy-2-hydroxybenzoic acid, 3-(3-carboxypropyl-1-oxy)-2-hydroxybenzoic acid, 4-(3-carboxypropyl-1-oxy)benzoic acid, 4-(3-carboxypropyl-1-oxy)-2-hydroxybenzoic acid, 4-(3-carboxypropyl-1-oxy)-2-methoxybenzoic acid, 5-(3-carboxypropyl-1-oxy)-2-hydroxybenzoic acid, 4-(5-carboxypentyl-1-oxy)-2-hydroxybenzoic acid, 6-(3-carboxypropyl-1-oxy)-2-hydroxybenzoic acid, 4-(10-carboxydecane-1-oxy)-2-hydroxybenzoic acid, 4-(10-carbamoyldecane-1-oxy)-2-hydroxybenzoic acid, 4-(4-hydroxybutyl-1-oxy)benzoic acid, 4-(4-hydroxybutyl-1-oxy)-2-hydroxybenzoic acid, 4-(4-acetoxybutyl-1-oxy)benzoic acid, 4-(4-acetoxybutyl-1-oxy)-2-hydroxybenzoic acid, 4-(3-ethoxycarbonylpropyl-1-oxy)-2-hydroxybenzoic acid, 3-(2,3-dihydroxypropyl-1-oxy)-2-hydroxybenzoic acid, 4-(4-methoxybutyl-1-oxy)-2-hydroxybenzoic acid, 4-(2,3-dihydroxypropyl-1-oxy)-2-hydroxybenzoic acid, 4-carboxymethyloxy-2-hydroxybenzoic acid, 3-(3-carboxypropyl-1-oxy)-2-hydroxybenzoic acid, 4-(3-carboxypropyl-1-oxy)-2-hydroxybenzoic acid, 5-(3-carboxypropyl-1-oxy)-2-hydroxybenzoic acid, 6-(3-carboxypropyl-1-oxy)-2-hydroxybenzoic acid, 4-(5-carboxypentyl-1-oxy)-2-hydroxybenzoic acid, 4-(4-hydroxybutyl-1-oxy)-2-hydroxybenzoic acid, 4-(10-carboxydecane-1-oxy)-2-hydroxybenzoic acid, hydroxytrimethyl cyclohexanes (e.g., monosaccharide glycoside, disaccharide glycoside or trisaccharide glycoside of, for example, 2-hydroxy-4-(2,2,6-trimethyl-1-yl-cyclohexane)butane, 4-(2,2,6-trimethyl-1-yl-cyclohexane)-1-butene, 4-(2,2,6-trimethyl-1-yl-cyclohexane)-2-butene, 4-(2,2,6-trimethyl-1-yl-cyclohexane)butane, 3-methyl-3-hydroxy-5-(2,2,6-trimethyl-1-yl-cyclohexane) pentane, 3-methyl-1-hydroxy-5-(2,2,6-trimethyl-1-yl-cyclohexane)pentane, 3-methyl-5-(2,2,6-trimethyl-1-yl-cyclohexane)pentane, 3-methyl-1-hydroxy-5-(2,2,6-trimethyl-1-yl-cyclohexane)-3-pentene, 3-methyl-3-hydroxy-5-(2,2,6-trimethyl-1-yl-cyclohexane)-1-pentene, 3-methyl-1-hydroxy-5-(2,2,6-trimethyl-1-yl-cyclohexane)-2-pentene, and 2-hydroxy-4-(2,2,6-trimethyl-1-yl-cyclohexane)butane), escinol, monosaccharide glycoside, disaccharide glycoside or trisaccharide glycoside of para-hydroxycinnamic acid-4-(2,2,6-trimethyl-yl-cyclohexane)-2-butyl ester, onjisaponin, Ophiopogonis saponin, ruscogenin, sericoside, asiaticoside, hederin, senegin, 4-(2,2,6-trimethyl-1-yl-cyclohexane)-2-keto-butane, 4-(2,2,6-trimethyl-1-yl-6-cyclohexene)-2-keto-butane, 4-(2,2,6-trimethyl-1-yl-cyclohexane)-2-keto-3-butene, 4-(2,2,6-trimethyl-1-yl-6-cyclohexene)-2-keto-3-butene(beta-ionone), L-p-hydroxyphenylglycine, D-p-hydroxyphenylglycine, N-benzyloxycarbonyl-L-p-hydroxyphenylglycine, N-benzyloxycarbonyl-D-p-hydroxyphenylglycine, N-benzoyl-L-p-hydroxyphenylglycine, N-benzoyl-D-p-hydroxyphenylglycine, N-(p-methoxybenzoyl)-L-p-hydroxyphenylglycine, N-(p-methoxybenzoyl)-D-p-hydroxyphenylglycine, N-(p-hydroxybenzoyl)-L-p-hydroxyphenylglycine, N-(p-hydroxybenzoyl)-D-p- hydroxyphenylglycine, N-acetyl-L-p-hydroxyphenylglycine, N-acetyl-D-p-hydroxyphenylglycine, N-acetyl-L-p-hydroxyphenylglycine ethyl ester, N-acetyl-D-p-hydroxyphenylglycine ethyl ester, N-acetyl-L-p-hydroxyphenylglycine amide, N-acetyl-D-p-hydroxyphenylglycine amide, L-p-methoxyphenylglycine, D-p-methoxyphenylglycine, L-p-methoxyphenylglycine hydrochloride, D-p-methoxyphenylglycine hydrochloride, 4-hydroxy-3-methoxy-L-phenylglycine, 4-hydroxy-3-methoxy-D-phenylglycine, L-p-hydroxyphenylglycine ethyl amide, D-p-hydroxyphenylglycine ethyl amide, N-tert-butoxycarbonyl-L-p-hydroxyphenylglycine, N-tert-butoxycarbonyl-D-p-hydroxyphenylglycine, N-tert-butoxycarbonyl-L-p-methoxyphenylglycine, N-tert-butoxycarbonyl-D-p-methoxyphenylglycine, N-9-fluorenylmethyloxycarbonyl-L-p-methoxyphenylglycine, N-9-fluorenylmethyloxycarbonyl-D-p-methoxyphenylglycine, N-9-fluorenylmethyloxycarbonyl-L-p-methoxyphenylglycine benzyl ester hydrochloride, N-9-fluorenylmethyloxycarbonyl-D-p-methoxyphenylglycine benzyl ester hydrochloride, L-p-hydroxyphenylglycine amide, D-p-hydroxyphenylglycine amide, L-p-hydroxyphenylglycine allyl ester p-toluenesulfonate, D-p-hydroxyphenylglycine allyl ester p-toluenesulfonate, L-p-hydroxyphenylglycine benzyl ester p-toluenesulfonate, D-p-hydroxyphenylglycine benzyl ester p-toluenesulfonate, L-p-hydroxyphenylglycine ethyl ester, D-p-hydroxyphenylglycine ethyl ester, L-p-hydroxyphenylglycine ethyl ester hydrochloride, D-p-hydroxyphenylglycine ethyl ester hydrochloride, L-p-hydroxyphenylglycine methyl ester, and D-p-hydroxyphenylglycine methyl ester, 1,3-diallylindane-2-carboxylic acids, stachybocins, pheophorbide derivatives, eleutherin, isoeleutherin or 4-beta-hydroxyisoeleutherin, eleutherinol, spiroketal derivatives (e.g., 2-(2,4-hexadiynylidene)-1,6-dioxaspiro[4.5]deca-3-ene, 2-(2-hexynylidene)-1,6-dioxaspiro[4.4]nona-3-ene, 2-((4-methylphenyl)methylidene)-6,6-dioxaspiro[4.4]nona-3-en e, 2-(2-hexenylidene)-6,6-dioxaspiro[4.5]deca-3-ene, 2-(2-hexenylidene)-1,6-dioxaspiro[4.4]nona-3-ene, 2-hexyl-1,6-dioxaspiro[4.4]nonane, 2-(2-hexenyl)-1,6-dioxaspiro[4.4]nonane, 2-(2-hexynyl)-1,6-dioxaspiro[4.4]nonane, 2-pentyl-1,6-dioxaspiro[4.4]nonane, 1,6-dioxaspiro[4.4]nonane, 1,6-dioxaspiro[4.5]decane, 1,7-dioxaspiro[5.5]undecane, 2,3-benzo-4,4-dimethyl-1,6-dioxaspiro[4.4]nonane, 3,4-benzo-2-pentyl-1,6-dioxaspiro[4.4]nonane, 3,4-benzo-2-hexyl-1,6-dioxaspiro[4.4]nonane, 3,4-benzo-2-octyl-1,6-dioxaspiro[4.4]nonane, 2-hexyl-9,9-dimethyl-1,6-dioxaspiro[4.4]nonane, and 2-(2,4-hexadiynylidene)-1,6-dioxaspiro[4.4]nona-3-ene), malvalic acid, phosphonic acid derivatives or salts thereof, aspergillomarasmine, aminophosphonic acid derivatives or salts thereof, diphenhydramine or salts thereof, pregnenolone or derivatives thereof, lutein, farnesyl isopropanol derivatives, hexahydrofarnesyl acetone, 4-benzoylamino-2-hydroxybenzoic acid, 5-benzoylamino-2-hydroxybenzoic acid, 4-benzoylaminobenzoic acid, 4-(1-naphthoylamino)-2-hydroxybenzoic acid, 5-(1-naphthoylamino)-2-hydroxybenzoic acid, 4-(2-naphthoylamino)-2-hydroxybenzoic acid, 5-(2-naphthoylamino)-2-hydroxybenzoic acid, 4-(1-naphthoylamino)benzoic acid, 4-(2-naphthoylamino)benzoic acid, 4-phenylaminocarbonyl benzoic acid, 4-phenylaminocarbonyl-2-hydroxybenzoic acid, 5-phenylaminocarbonyl-2-hydroxybenzoic acid, 4-(1-naphthylaminocarbonyl)benzoic acid, 4-(1-naphthylaminocarbonyl)-2-hydroxybenzoic acid, 5-(1-naphthylaminocarbonyl)-2-hydroxybenzoic acid, 4-(2-naphthylaminocarbonyl)benzoic acid, 4-(2-naphthylaminocarbonyl)-2-hydroxybenzoic acid, 5-(2-naphthylaminocarbonyl)-2-hydroxybenzoic acid, hexahydrofarnesyl isopropanol derivatives, borneol-p-hydroxycinnamic acid ester glucoside, borneol-p-hydroxycinnamic acid ester maltoside, borneol-p-hydroxycinnamic acid ester maltotrioside, cinnamic acid-4-(2,2,6-trimethyl-yl-cyclohexane)-2-butyl ester derivatives, 2,4-dihydroxybenzophenone, 1-(2,4-dihydroxyphenyl)-ethanone(2',4'-dihydroxyacetophenone), 1-(2,4-dihydroxyphenyl)-1-propanone (21,4'-dihydroxypropiophenone), 1-(2,4-dihydroxyphenyl)-1-butanone, 1-(2,4-dihydroxyphenyl)-1-pentanone, 1-(2,4-dihydroxyphenyl)-1-hexanone, 1-(2,4-dihydroxyphenyl)-1-heptanone, 1-(2,4-dihydroxyphenyl)-1-octanone, 1-(2,4-dihydroxyphenyl)-1-nonanone, 1-(2,4-dihydroxyphenyl)-1-decanone, 1-(2,4-dihydroxyphenyl)-1-undecanone, 1-(2,4-dihydroxyphenyl)-1-dodecanone, 1-(2,4-dihydroxyphenyl)-1-tetradecanone, 1-(2,4-dihydroxyphenyl)-1-hexadecanone, 1-(2,4-dihydroxyphenyl)-1-octadecanone, 1-(2-hydroxy-4-methoxyphenyl)-ethanone(2'-hydroxy-4'-methoxy acetophenone), 1-(2-hydroxy-4-methoxyphenyl)-1-propanone(2'-hydroxy-4'-meth oxypropiophenone), 1-(2-hydroxy-4-methoxyphenyl)-1-butanone, 1-(2-hydroxy-4-methoxyphenyl)-1-pentanone, 1-(2-hydroxy-4-methoxyphenyl)-1-hexanone, 1-(2-hydroxy-4-methoxyphenyl)-1-heptanone, 1-(2-hydroxy-4-methoxyphenyl)-1-octanone, 1-(2-hydroxy-4-methoxyphenyl)-1-nonanone, 1-(2-hydroxy-4-methoxyphenyl)-1-decanone, 1-(2-hydroxy-4-methoxyphenyl)-1-undecanone, 1-(2-hydroxy-4-methoxyphenyl)-1-dodecanone, 1-(2-hydroxy-4-methoxyphenyl)-1-tetradecanone, 1-(2-hydroxy-4-methoxyphenyl)-1-hexadecanone, 1-(2-hydroxy-4-methoxyphenyl)-1-octadecanone, 1-(4-hydroxy-2-methoxyphenyl)-ethanone(4'-hydroxy-2'-methoxy acetophenone), 1-(4-hydroxy-2-methoxyphenyl)-1-propanone(4'-hydroxy-2'-meth oxypropiophenone), 1-(2,4-dimethoxyphenyl)-ethanone(2',4'-dimethoxyacetophenone 1-(2,4-dimethoxyphenyl)-1-propanone(2',4'-dimethoxypropiophenone), lactone derivatives (e.g., 1,6-dioxaspiro[4.4]nonane-2,7-dione, 1,6-dioxaspiro[4.5]decane-2,7-dione, 4-tridecanolide, 4-dodecanolide, 4-undecanolide, 4-decanolide, 4-nonanolide, 4-octanolide, 4-heptanolide, 5-dodecanolide, 5-undecanolide, 5-decanolide, 5-nonanolide, 5-octanolide, 2-undecen-4-olide, 2-decen-4-olide, 2-nonen-4-olide, 2-hepten-4-olide, 2-undecen-5-olide, 2-decen-5-olide, 2-nonen-5-olide, 2-octen-5-olide, 4-methyl-4-dodecanolide, 4-methyl-4-undecanolide, 4-methyl-4-decanolide, 4-methyl-4-nonanolide, 4-methyl-4-heptanolide, 5-methyl-5-dodecanolide, 5-methyl-5-undecanolide, 5-methyl-5-decanolide, 5-methyl-5-nonanolide, 5-methyl-5-octanolide, 2-methoxycarbonyl-4-dodecanolide, 2-methoxycarbonyl-4-undecanolide, 2-methoxycarbonyl-4-decanolide, 2-methoxycarbonyl-4-nonanolide, 2-methoxycarbonyl-4-heptanolide, 2-methoxycarbonyl-5-undecanolide, 2-methoxycarbonyl-5-decanolide, 2-methoxycarbonyl-5-nonanolide, 2-methoxycarbonyl-5-octanolide, 2-allyl-4-undecanolide, 2-allyl-5-decanolide, 2-allyl-4-nonanolide, 2-pentyl-4-undecanolide, 2-pentyl-4-nonanolide, 2-methyl-4-undecanolide, 2-methyl-4-nonanolide, 2-(4-hydroxybutyl)-4-undecanolide, 2-(4-hydroxybutyl)-4-nonanolide, 2-(4-hydroxybutyl)-5-decanolide, 5-propyloxy-4-pentanolide, 5-allyloxy-4-pentanolide, 5-(2-hydroxyethoxy)-4-pentanolide, 8-hydroxy-4-octanolide, 6-propyloxy-5-hexanolide, 6-allyloxy-5-hexanolide, 6-(2-hydroxyethoxy)-5-hexanolide, and 9-hydroxy-5-nonanolide), echinomycin, irifloental, iripallidal, 2'-8-C-glucosyl-7-methylaloesol coumaroyl ester, 2'-8-C-glucosyl-7-methylaloesol cinnamoyl ester, chloropyramine, *Pimpinella Anisum* extract, *Aloe arborescens* extract, *Reynoutria japonica* (HU ZHANG) extract, *Daphne pseudo-* mezereum extract, *Cassia obtusifolia* extract, JUE MING ZI (*Cassia obtusifolia* seed; Cassiae Semen) extract, HUANG QI (*Astragalus mongholicus* root; Astragali Radix) extract, *Astragalus membranaceus* extract, *Trichosanthes bracteata* (*Trichosanthes* root) extract, *Xanthium strumarium* (CHANG ER ZI) extract, *Gastrodia elata* (TIAN MA) extract, *Pyracantha fortuneana* extract, *Polygonum sachalinense* extract, WU YAO (*Lindera strychnifolia* root; Linderae Radix) extract, pumpkin extract, *Typha latifolia* (PU HUANG) extract, *Euphorbia kansui* (GAN SUI) extract, *Agrimonia pilosa* var. *japonica* (XIAN HE CAO) extract, *Lindera umbellata* extract, *Saxifraga fusca* var *kikubuki* extract, sisal (*Agave sisalana*) extract, *Clematis chinensis* extract, *Clematis chinensis* extract, *Clematis chinensis* (WEI LING XIAN) extract, *Prunus lannesiana* var. *speciosa* extract, *Prunus sargentii* extract, *Prunus incisa* extract, *Prunus nipponica* Matsumura extract, *Prunus subhirtella* extract, *Prunus lannesiana* extract, *Aster tataricus* (ZI WAN) extract, *Trachycarpus fortunei* extract, *Iris florentina* L. extract, *Clematis terniflora* (DA LIAO) extract, *Magnolia salicifolia* (XIN YI HUA) extract, *Saxifraga fortunei* var. *incisolobata* extract, *Oenothera tetraptera* extract, TU SI ZI (*Cuscuta chinensis* Lam. seed) extract, *Cuscuta australis* extract, *Cuscuta japonica* extract, *Artemisia absinthium* L. extract, *Achillea alpina* extract, *Dictamnus dasycarpus* (BAI XIAN PI) extract, *Anethum graveolens* extract, *Fallopia japonica* var. *hachidyoensis* extract, *Tribulus terrestris* extract, *Pyrrosia lingua* (SHI WEI) extract, *Typha angustifolia* L. (XIANG PU) extract, *Angelica dahurica* extract, *Buddleja Americana* L. extract, *Brickellia cabanillesy* extract, *Artemisia* fukudo extract, *Convolvulus arvensis* extract, sandalwood extract, *Ganoderma lucidum* (LING ZHI) extract, *Leonurus japonicus* (YI MU CAO) extract, *Salix gilgiana* extract, *Salix chaenomeloides* extract, *Salix gracilistyla* extract, *Salix integra* extract, *Salix kinuyanagi* extract, *Salix koriyanagi* extract, *Salix matsudana* cv. *Tortuosa* extract, *Salix Reinii* extract, *Salix sieboldiana* extract, *Toisusu urbaniana* extract, *Salix schwernii* extract, *Salix vulpina* extract, *Populus maximowiczii* extract, *Myrica rubra* (YANG MEI PI) extract, *Agave americana* extract, *Agave americana* var. *marginata* extract, *Agave americana* 'Marginata' extract, *Edgeworthia chrysantha* extract, *Enteromorpha* (green layer) extract, *Enteromorpha linza* extract, *Enteromorpha prolifera* extract, *Enteromorpha compressa* extract, *Enteromorpha intestinalis* extract, *hosoeda aonori* extract, *Laminaria* (sea tangle) extract, *Laminaria japonica* extract, *Laminaria ochotensis* extract, *Laminaria religiosa* extract, *Laminaria angustata* extract, *Undaria pinnatifida* extract, *Undaria undaroides* extract, *Undaria peterseniana* extract, *Hizikia fusiformis* extract, *Fucus evanescens* extract, *Padina arborescens* extract, *Padina australis* extract, *kirebanoumiuchiwa* extract, *akabaumiuchiwa* extract, *Padina crassa* extract, *Padina japonica* extract, *Padina* minor extract, *etsukiumiuchiwa* extract, *Eucheuma serra* extract, *Eucheuma amakusaense* extract, *Eucheuma* extract, *byakushinkirinsai* extract, *Chondrus ocellatus* extract, *Chondrus verrucosus* extract, *Chondrus nipponicus* extract, *Chondrus pinnulatus* extract, *Chondracanthus tenellus* extract, *Chondracanthus teedii* extract, *Chondracanthus intermedius* extract, *Dictyopteris latiuscula* extract, *uraboshiyahazu* extract, *Padina arborescens* extract, *Sphaerotrichia divaricata* extract, *Cymathaere* extract, *Cymathaere japonica* extract, *Sargassum hemiphyllum* extract, *nagashimamoku* extract, *Sargassum filicinum* extract, *Sargassum sagamianum* extract, *Sargassum nigrifolium* extract, *Sargassum piluliferum* extract, *tatsukuri* extract, *Sargassum patens* extract, *Sargassum thunbergii* extract, *Sargassum ringgoldianum* extract, *Sargassum confusum* extract, *Sargassum kjellmanianum* extract, *Sargassum siliquastrum* extract, *Sargassum serratifolium* extract, *Sargassum giganteifolium* extract, *Grateloupia filicina* extract, *Halymenia agardhii* extract, *kuronurakusa* extract, *Halymenia acuminata* extract, *Carpopeltis affinis* extract, *Gracilaria gigas* extract, *Ceratodictyon spongiosum* extract, *Lomentaria catenata* extract, *himefushitsunagi* extract, *Lomentaria okamurae* extract, *Laurencia intermedia* extract, *Laurencia undulata* extract, *Laurencia pinnata* extract, *Laurencia brongniartii* extract, *Odonthalia corymbifera* extract, *Tila* extract, *Camotede azafran* extract, *Jamaica* extract, *Poleo verde* extract, *Navo negro* extract, *Schisandra chinensis* extract, *Schisandra nigra* extract, and *Kadsura japonica* extract.

Optical Brighteners

The topical cosmetic compositions may optionally further comprise one or more optical brighteners. Optical brighteners are described in *Fluorescent Whitening Agent, Encyclopedia of Chemical Technology*, Kirk-Othmer, Vol. 11, pp. 227-241, 4th edition, 1994, Wiley, which is hereby incorporated by reference herein in its entirety. Optical brighteners can be defined more particularly as compounds which absorb in the UVA range between 300 and 390 nm and re-emit essentially between 400 and 525 nm. Suitable optical brighteners can comprise or consist of, but are not limited to, one or more of stilbene derivatives (e.g., sodium 4,4'-bis[(4,6-dianilino-1,3,5-triazin-2-yl)amino]stilbene-2,2'-disulphonate), coumarin derivatives, oxazole and benzoxazole derivatives (e.g., 2,5-thiophenediylbis(5-tert-butyl-1,3-benzoxazole)) and imidazole-derivatives. Amounts of optical brighteners generally range from about 0.1% to about 5.0%, based on total weight of the composition. A suitable optical brightener is oxazole.

Anti-Inflammatory Agents

The topical cosmetic compositions may optionally further comprise one or more anti-inflammatory agents. Suitable anti-inflammatory agents useful in this regard can comprise or consist of, but are not limited to, one or more of propionic acid derivatives, acetic acid derivatives, fenamic acid derivatives, biphenylcarboxylic acid derivatives, oxicams, acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen, bucloxic acid, apazone, bromfenac, celecoxib, diclofenac, difenpiramide, diflunisal, etodolac, flufenamic acid, indomethacin, ketorolac, meclofenamate, mefenamic acid, meloxicam, nabumetone, phenylbutazone, piroxicam, butibufen, rofecoxib, salicylic acid, sulindac, tolmetin, ketorolac tromethamine, antihistaminic agents, diphenhydramine, chlorpheniramine, diphenhydramine hydrochloride, chlorpheniramine maleate, corticosteroids, alclometasone, dexamethasone, flumethasone, hydrocortisone, hydrocortisone-21-monoesters, hydrocortisone-21-acetate, hydrocortisone-21-butyrate, hydrocortisone-21-propionate, hydrocortisone-21-valerate, hydrocortisone-17,21-diesters, hydrocortisone-17,21-diacetate, hydrocortisone-17-acetate-21-butyrate, hydrocortisone-17,21-dibutyrate, prednisolone, methylprednisolone, betamethasone benzoate, betamethasone dipropionate, clobetasol propionate, diflorasone diacetate, fluocinonide, fluticasone propionate, mometasone furoate, triamcinolone acetonide, topical corticosteroids, hydroxyltriamcinolone, alpha-methyl dexamethasone, dexamethasone-phosphate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, medrysone, amcinafel, amcinafide, betamethasone, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisone, beclomethasone dipropionate, triamcinolone, isoxicam, tenoxicam, sudoxicam, CP-14,304, salicylates, disalcid, benorylate, trilisate, safapryn, solprin, fendosal, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acid, pyrazoles, phenylbutazone, oxyphenbutazone, feprazone, azapropazone, trimethazone, candelilla wax, bisabolol, alpha bisabolol, *aloe* vera, plant sterols, phytosterol, Manjistha, Guggal, kola extract, chamomile, red clover extract, *Piper methysticum* extract, *Bacopa monieri* extract, sea whip extract, and mixtures thereof.

Anti-Microbial Agents

Non-limiting examples of suitable anti-microbial and anti-fungal agents useful in this regard include, but are not limited to, beta-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, zinc erythromycin, erythromycin estolate, erythromycin steaerate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mendelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xyleneol, nystatin, tolnaftate, clotrimazole, benzoyl peroxide, azelaic acid, ethyl acetate, meclocycline, lincomycinics, tetracyclinics, sulfur-based antibiotics, sulfonamides, mupirocin, magainin I, magainin II, lincomycin, (6,8-dideoxy-6-[[(1-methyl-4-propyl-2-pyrrolidinyl)-carbonyl]amino]-1-thio-L-threo-alpha-D-galacto-octopyranoside), 7-chloro-6,7,8-trideoxy-6-[[(1-methyl-4-propyl-2-pyrrolidinyl)carbonyl]-amino]-1-thio-L-threo-alpha-D-galacto-octopyranoside, (4-(dimethylamino)-1,4,4-alpha,5,5-alpha, 6,11,12-alpha-octahydro-3,6,12,12-alpha-pentahydroxy-6-methyl-1,11-dioxo-2-naphthacene-carboxamide), chlortetracycline, demeclocycline, rolitetracycline, sulfacetamide, sulfabenzamide, sulfadiazine, sulfadoxine, sulfamerazine, sulfamethazine, sulfamethizole, sulfamethoxazole, sulfacetamide sodium, amphotericin B, benzoic acid, butenafine, butenafine HCl, butoconazole, butoconazole nitrate, caprylic acid, chloroxylenol, ciclopirox, clotrimazole, econazole, econazole nitrate, fluconazole, itraconazole, ketoconazole, miconazole, miconazole nitrate, naftifine, naftifine hydrochloride, nystatin, oxiconazole, oxiconazole nitrate, salicylic acid, selenium, selenium sulfide, sulconazole, sulconazole nitrate, terbinafine, terbinafine hydrochloride, terconazole, tioconazole, undecylenic acid, acitretin, alclometasone dipropionate, anthralin, azathioprine, calcipotriene, calcitriol, colchicine, cyclosporine, methoxsalen, retinoids, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, azelaic acid, arachidonic acid, benzethonium chloride, benzalkonium chloride, boric acid, 8-quinolinol benzoate, secondary amyltricresols, cetylpyridinium chloride, chlorothymol, and 8-hydroxyquinoline sulfate, pharmaceutically or cosmetically acceptable salts thereof, and mixtures thereof.

Anti-Wrinkle and Anti-Atrophy Agents

The topical cosmetic compositions may optionally further comprise one or more anti-wrinkle and/or anti-atrophy agents. Suitable non-limiting examples of anti-wrinkle and/or anti-atrophy agents useful in this regard can include anti-wrinkle and/or anti-atrophy agents that can comprise or consist of one or more of cis and trans retinoic acid, retinol, retinol esters, salicylic acid, sulfur-containing D and L amino acids, N-acetyl derivatives sulfur-containing D and L amino acids, N-acetyl-L-cystein, thiols, ethane thiol, alpha-hydroxy acids, glycolic acid, lactic acid, phytic acid, lipoic acid, lysophosphatidic acid, skin peel agents, phenol, pharmaceutically or cosmetically acceptable salts thereof, and mixtures thereof.

Anti-Acne Agents

The topical cosmetic compositions may optionally further comprise one or more anti-acne agents. Suitable non-limiting examples of anti-acne agents useful in this regard can include anti-acne agents that can comprise or consist of one or more of keratolytics, salicylic acid (o-hydroxybenzoic acid), 5-octanoyl salicylic acid, resorcinol, retinoids, cis and trans retinoic acid, sulfur-containing D and L amino acids, N-acetyl sulfur-containing D and L amino acids, N-acetyl-L-cysteine, lipoic acid, sebostats, flavonoids, bile salts, scymnol sulfate, deoxycholate, cholate, adapalene, azelaic acid, benzoyl peroxide, clindamycin, clindamycin phosphate, doxycycline, erythromycin, norgestimate, organic peroxides, isotretinoin, tretinoin, sulfacetamide sodium, tazarotene, pharmaceutically or cosmetically acceptable salts thereof, and mixtures thereof.

Methods of Treatment

In an embodiment, the present subject matter relates to a method of lightening skin pigmentation in a subject, comprising topically administering to skin of a subject in need thereof, a therapeutically effective amount of the topical cosmetic composition in accordance with the subject matter described herein.

In another embodiment, the present subject matter relates to a method of treating a skin disorder or condition in a subject, comprising topically administering to skin of a subject in need thereof, a therapeutically effective amount of the topical cosmetic composition in accordance with the subject matter described herein. The skin disorder or condition can be a disorder or condition associated with undesirable skin pigmentation.

In another embodiment, the present subject matter relates to a method of lightening skin pigmentation in a subject or treating a skin disorder or condition in a subject, comprising topically administering for at least once per day for at least three days, for at least five days, for at least seven days, for at least ten days, or for at least fourteen days, to skin of a subject in need thereof, a therapeutically effective amount of the topical cosmetic composition in accordance with the subject matter described herein. In this regard, after three days, five days, seven days, ten days, or fourteen days, respectively, of administration of the present topical compositions the skin is visibly altered.

In an embodiment, the present subject matter relates to a method of lightening skin pigmentation in a subject or treating a skin disorder or condition in a subject, comprising topically administering for at least once per day for at least three weeks to skin of a subject in need thereof, a therapeutically effective amount of the topical cosmetic composition in accordance with the subject matter described herein, wherein after three weeks the skin is visibly lightened.

The present topical cosmetic compositions are effective in treating a variety of skin disorders or conditions characterized by undesirable skin pigmentation. Non-limiting examples of such disorders and/or conditions can include regional hyperpigmentation caused by melanocytic hyperactivity such as idiopathic melasma occurring during pregnancy (mask of pregnancy or chloasma) or secondary to estrogen-progesterone contraception; local hyperpigmentation caused by benign melanocytic hyperactivity and proliferation such as lentigo senilis, known as liver spots; accidental hyperpigmentation such as post-lesional photosensitization and scarring; freckles; malpigmentation; and certain forms of leukoderma such as vitiligo where, if the injured skin cannot be repigmented, the residual zones of normal skin are lightened or depigmented to impart a homogeneous color to the entire skin. Skin can be treated according to the presently described methods for purely cosmetic lightening of areas, for example, large areas, of skin whose pigmentation, although undesired, is adequate for the individual skin type. In an embodiment, the skin disorder or condition to be treated according to the present methods is undesired skin pigmentation. The administration of the present topical cosmetic composition to areas of the skin that contain undesired pigmentation, lightens those areas. Accordingly, the present methods lighten areas of the skin to which the present topical cosmetic compositions are administered.

Suitable skin areas for treatment and/or lightening in accordance with the subject matter described herein can include thin skin areas including for example areas of skin on the face, neck, and/or hands. The present compositions and methods as described herein are suitable for use in both men and women, and are suitable for use on all skin types including dry skin types, normal skin types, and greasy skin types.

In a further embodiment, the present subject matter relates to a method of treating a skin disorder or condition in a subject, or to a method of lightening skin pigmentation in a subject, wherein topically administering to skin comprises administering at least once per day or at least twice per day for a period of at least two weeks, at least 3 weeks, or at least 4 weeks, wherein skin pigmentation is lightened. Administering at least once per day can comprise administering once in the morning or in the evening. Administering at least twice per day can comprise administering once in the morning and once in the evening.

Methods of Production

Various formulations of the present topical cosmetic compositions in accordance with the presently described subject matter can be readily produced by the skilled artisan according to known methods of producing such formulations including for example, a cream, a gel, a serum, a lotion, or other formulation described herein, without undue experimentation.

A process for producing a cream or emulsion formulation can comprise separately producing an aqueous phase and an oil phase, adding the oil phase to the aqueous phase, for example with mixing and/or homogenization (with high shear), to an emulsion. After the emulsion is produced, one or more of the following components can be optionally added thereto, for example, in the following order, to produce the final emulsion or cream: one or more skin lightening actives; one or more pH adjusters; one or more emollients; one or more skin lightening actives; one or more sunscreen actives; one or more thickening agents; one or more antioxidants; and one or more fragrances. Prior to forming the emulsion, the aqueous phase and the oil phase can be separately heated to a temperature of from about 70° C. to about 99° C.; from about 75° C. to about 95° C.; from about 80° C. to about 90° C.; or about 85° C. After heating the oil phase can be slowly added to the aqueous phase, for example, with mixing and high shear homogenization. The resultant emulsion can then be cooled while maintaining mixing and high shear homogenization, for example, to a temperature of from about 47° C. to about 27° C.; from about 42° C. to about 30° C.; from about 39° C. to about 35° C.; or about 37° C. Thereafter, one or more of the above-described optional components can then be added to the cooled emulsion, for example, with mixing and/or high shear homogenization. The produced emulsion or cream can have a pH of from about 4.5 to 6.5 and/or a viscosity of from about 5,000 cP to about 15,000 cP and/or a density of from about 1.01 to about 1.06.

Further contemplated as within the scope of the present subject matter are topical cosmetic compositions produced according to the above-described processes. If produced according to these processes, these compositions exhibit chemical and physical stability suitable for topical administration.

The topical cosmetic compositions produced according to these processes can be placed in a suitable containment vessel comprising a product contact surface composed of a material selected from the group consisting of glass, plastic, steel, stainless steel, aluminum, Teflon, polymeric structure, ceramic structure, alloys, and mixtures thereof. These containment vessels are used to facilitate manufacturing, handling, processing, packaging, storage, and administration of said topical cosmetic composition. Suitable containment vessels in this regard can be selected from the group consisting of plastic tubes, bottles, metal tubes, and any combination thereof.

Routes of Administration/Dosage

To be effective, the route of administration for topical cosmetic compositions used in the present methods must readily affect the target skin areas. Effective results in most cases are achieved by topical application of a thin layer over the affected area, or the area where one seeks to achieve the desired effect. Effective results can be achieved with application rates from one application every two or three days to four or more applications per day.

Appropriate dosage levels for the active agents contemplated in the present topical cosmetic compositions and methods are well known to those of ordinary skill in the art and are selected to maximize the treatment of the above skin conditions. Dosage levels on the order of about 0.001 mg to about 5,000 mg per kilogram body weight of the skin lightening active components are known to be useful in the treatment of the diseases, disorders, and conditions contemplated herein. Typically, this effective amount of the skin lightening active components will generally comprise from about 0.001 mg to about 100 mg per kilogram of patient body weight per day. Moreover, it will be understood that this dosage of ingredients can be administered in a single or multiple dosage units to provide the desired therapeutic effect.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

The present compositions may be given in a single dose or multiple doses daily. In an embodiment, the present topical cosmetic compositions are given from one to four times daily. Starting with a low dose once or twice daily and slowly working up to higher doses if needed is a strategy. The amount of active ingredients that may be combined with the carrier materials to produce a single dosage form will vary depending upon the host treated, the nature of the disease, disorder, or condition, and the nature of the active ingredients. In an embodiment, the topical cosmetic compositions may be topically applied once or multiple times per day. In an embodiment, the present topical cosmetic compositions are topically applied from one to four times daily. For example, starting with once daily and progressing to more frequent applications, if needed, is one strategy.

In an embodiment, the present topical cosmetic compositions are topically applied from one to four times daily, for example, in the morning, at noon, in the afternoon, and/or in the evening.

In an embodiment, the topical cosmetic compositions as described herein can be administered once or multiple times per day for a period of time of at least one week, for a period of at least two weeks, for a period of at least four weeks, or for a period of at least eight weeks. The topical cosmetic compositions can be administered once or multiple times per day for a period of time of up to one year, of up to six months, of up to three months, or of up to two months.

It is understood, however, that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal cosmetic formulations can be determined by one skilled in the art depending upon considerations such as the particular ingredients and the desired dosage. See, for example, *Remington's Pharmaceutical Sciences*, 18th ed. (1990, Mack Publishing Co., Easton, Pa. 18042), pp. 1435-1712, and "Harry's Cosmeticology", 8th ed. (2000, Chemical Publishing Co., Inc., New York, N.Y. 10016), the disclosure of each of which is hereby incorporated by reference herein in its entirety. Such formulations may influence the physical state, stability, rate of in vivo release, and rate of in vivo clearance.

In an embodiment, the present topical cosmetic composition in accordance with the subject matter described herein may be a gel cream packaged in, for example, a tube, or a serum packaged in, for example, a non-aerosol non-foaming pump container or bottle, wherein the amount of the composition contained in the container can be in the range of from about 10 gm to about 60 gm, between about 20 gm and about 50 gm, or about 30 gm, or about 40 gm.

Single dosage kits and packages containing once per day amount of composition may be prepared. Single dose, unit dose, and once-daily disposable containers of the present compositions are contemplated as within the scope of the present subject matter.

The present topical cosmetic compositions in accordance with the subject matter described herein may be formulated for storage in a substantially non-reactive laminated package to enhance stability of the package. This method of storage provides enhanced package stability in comparison with other, paper-based packages.

The amount of composition per single packet may range be from about 0.1 ml to about 20.0 ml, between about 0.5 and about 5.0 ml, or between about 1 and about 3 ml.

In particular, the ability to formulate compositions capable of long term storage, without pre-mixing or compounding requirements prior to application is also contemplated. Specifically, the present compositions remain unexpectedly stable in storage for periods including between about 3 months and about 3 years, about 3 months and about 2.5 years, between about 3 months and about 2 years, between about 3 months and about 20 months, and alternately any time period between about 6 months and about 18 months.

In an embodiment, the presently described topical cosmetic formulation in accordance with the subject matter described herein remains stable for at least three years at a temperature of less than 30° C. In an embodiment, the presently described topical cosmetic formulation remains stable for at least two years at a temperature of less than or equal to 30° C. In an embodiment, the presently described topical cosmetic formulation remains stable for at least two years at a temperature of less than or equal to 25° C.

EXAMPLES

The following examples are illustrative of the present topical cosmetic compositions and are not intended to be limitations thereon. Any polymer molecular weights are mean average molecular weights. All percentages are based on the percent by weight of the final delivery system or formulation prepared unless otherwise indicated and all totals equal 100% by weight.

Example 1

The following example illustrates the clarifying efficacy of the present topical cosmetic composition as compared to a 2% hydroquinone composition, determined through colorimetry instrumental methodology.

In a monocentric, double-blind, comparative clinical trial over a period of six (6) weeks, the clarifying efficacy of each of two topical products was evaluated in the previously pigmented skin of 10 (ten) volunteers. Dermatological evaluations were performed at the beginning and the end of the study Skin color was measured by colorimetry, together with the photographic documentation, at T0, T07, T14, and T21. UVB pigmentation was induced in the previously pigmented skin of the volunteers through the use of a light emitting source, i.e., the solar simulator with Xenon arc light 601/300 W, produced by Solar Light CO.

A Minolta Chroma Meter CR400 through a standard color system CIE (The Commission Internacional de l'Eclairage) was used to determine the skin coloration. The color is expressed by a system of three-dimensional coordinates where the $L^*$ axis corresponds to skin luminosity, the $a^*$ axis corresponds to green and red colors, and the b* axis corresponds to blue and yellow colors.

The solar simulator with Xenon arc light 601/300 W, produced by Solar Light CO, was used as the light source. This equipment provides continuous light emission in the UVB and UVA spectrum, ranging between 290 and 400 nm. The device includes a set of lenses and filters that absorb or disperse irradiation lower than 320 nm or higher than 400 nm. The irradiation occurs through a set of 6 branches of optic fiber called "ports", programmed to apply pre-established individual doses of irradiation. Irradiation monitoring was performed using a Dose Controlling System (DCS), which includes a UVB irradiation detector and an electronic monitor. In this study, only three "ports" were used for each application site of the tested compositions.

Evaluated Samples

1. Hydroquinone 2% (positive control):

| Component | Function | % W/W |
| --- | --- | --- |
| Citric acid | pH adjuster | 0.08 |
| Purified water | vehicle | 67.08 |
| Benzophenone-3 | sunscreen active | 1.5 |
| Octyl methoxycinnamate | sunscreen active | 6 |
| Hydroquinone | lightening agent | 2 |
| Lanette | emulsifier | 13 |
| Sodium metabissulfite | antioxidant | 0.14 |
| Isopropyl palmitate | emollient | 5 |
| Propylene glycol | emollient | 5 |
| Methylparaben | preservative | 0.15 |
| Propylparaben | preservative | 0.05 |
| | | 100.0% |

2. The present topical cosmetic composition comprising:

| Component | Function | % W/W |
| --- | --- | --- |
| Purified water | carrier | 62.250 |
| Cetyl alcohol | thickening agent | 2.2 |
| Butylated hydroxytoluene | antioxidant | 0.050 |
| (C14-22 alcohols and C12-20 alkylglycoside) | emulsifier | 5 |
| Cyclopentasiloxane PEG/PPG-18/18 dimethicone | emollient | 1 |
| Cyclopentasiloxane dimethicone crosspolymer | emollient | 1 |
| Sodium EDTA | chelating agent | 0.2 |
| Bellis perennis flower extract | antioxidant/active | 5 |
| Phyllanthus embilica fruit extract | antioxidant/active | 2 |
| Licorice extract | antioxidant/active | 0.050 |
| Phenoxyethanol and methylisothiazolinone | preservative | 0.6 |
| Perfume | fragrance | 0.3 |
| Hydroxyethyl acrylate, Sodium acryloyldimethyltaurate copolymer, Squalane, and Polysorbate 60 | thickening agent | 5 |
| Sodium metabissulfite | antioxidant | 0.3 |
| Methylene bis-benzotriazolyl tetramethylphenol | sunscreen active | 5 |
| Ethylhexyl Methoxycinnamate | sunscreen active | 7.5 |
| Propylene glycol | emollient | 2 |
| Triethanolamine | pH adjuster | 0.55 |
| | | 100.0% |

Formulation:

Method of Manufacturing

1. In a suitable vessel disperse the Methylene bis-benzotriazolyl tetramethylphenol in a small quantity of Purified Water. Mix until uniform.
2. In a suitable vessel, blend until uniform the Cyclopentasiloxane PEG/PPG-18/18 dimethicone and Cyclopentasiloxane dimethicone crosspolymer.
3. In a suitable vessel, place the Propylene Glycol. Add and disperse the Licorice Extract. Mix until uniform.
4. In a suitable vessel disperse the *Phyllanthus Embilica* fruit extract in a small quantity of Purified Water. Mix until uniform.
5. In a suitable vessel disperse the Triethanolamine in a small quantity of Purified Water. Mix until uniform.
6. In a suitable vessel disperse the Sodium Metabisulfite in a small quantity of Purified Water. Mix until uniform.
7. To the main manufacturing vessel, add the remaining Purified Water While mixing, add and disperse the Sodium EDTA. Heat the contents to about 85° C.
8. To a suitable vessel, add the cetyl alcohol, C-14-22 alcohols and C-12-20 alkylglycoside, cetyl alcohol, Ethylhexyl methoxycinnamate, and Butylated Hydroxytoluene. Heat to about 85° C. and mix until uniform.
9. Add the mixture of Step 8 to the mixture of Step 7 with agitation. Mix until uniform.
10. While mixing, cool batch to about 37° C.
11. Add while mixing add the mixture of Step 4 and then add the mixture of Step 5. Mix until uniform.
12. Add while mixing Phenoxyethanol and Methylisothiazolinone.
13. While mixing add the mixture of Step 2, then the mixture from Step 3. Mix until uniform.
14. Add the *Belis Perennis* flower extract and mix until uniform.
15. While mixing add the mixture from Step 1 and mix until uniform.
16. Add the Hydroxyethyl acrylate, sodium acryloyldimethyltaurate copolymer, squalene and polysorbate 60. Mix until uniform.
17. While mixing add the mixture from Step 6. Mix until uniform.
18. While mixing add the Perfume. Mix until uniform.
19. This formulation has a pH ranging from 4.5-6.5; a viscosity ranging from 5,000 to 15,000 cP; and a density ranging from 1.01 to 1.06.

Alternative topical cosmetic composition comprising:

| Function | Component | % W/W |
| --- | --- | --- |
| 01. 1$^{st}$ Portion Purified Water | Vehicle | 46.470 |
| 02. 2$^{nd}$ Portion Purified Water | Vehicle | 5.000 |
| 03. 3$^{rd}$ Portion Purified Water | Vehicle | 5.000 |
| 04. 4$^{th}$ Portion Purified Water | Vehicle | 5.000 |
| 05. 5$^{th}$ Portion Purified Water | Vehicle | 2.000 |
| 06. Cetyl Alcohol | Thickener | 2.000 |
| 07. Butylhydroxytoluene | Antioxidant | 0.050 |
| 08. Disodium EDTA | Chelating Agent | 0.200 |
| 09. Sodium Metabisulfite | Antioxidant | 0.300 |
| 10. Ethylhexyl methoxycinnamate | Solar Filter | 7.500 |
| 11. Propylene Glycol | Solubilizer | 2.000 |
| 12. Triethanolamine 99W | Regulation of pH | 0.550 |
| 13. Methylene Bis-Benzotriazolyl Tetramethylbutylphenol (and) Decyl Glucoside (and) Xanthan Gum (and) Propylene glycol (and) Water (Ciba) | Solar Filter | 5.000 |
| 14. Cyclopentasiloxane/PEG/PPG-18/18 Dimethicone (Dow Corning) | Emollient | 2.000 |
| 15. Dimethicone Crosspolymer (and) Cyclomethicone (Dow Corning) | Emollient | 2.000 |
| 16. Hydroxyethyl Acrylate (and) Sodium Acryloyldimethyl Taurate Copolymer (and) Squalane (and) Polysorbate 60 (Chemyunion) | Thickener | 5.000 |
| 17. Phenoxyethanol (and) Methylisothiazolinone (Rohm & Haas) | Preservative | 0.570 |
| 18. C14/C22 Alcohol (and) C12/C20 Alkyl glucoside (Chemyunion) | Emulsifier | 2.000 |

-continued

| Function | Component | % W/W |
|---|---|---|
| 19. Extract of Licorice (Bioland Ltd.) | Active | 0.060 |
| 20. Extract of Bellis Perennis (Chemisches Laboratorium Dr. Kurt Richter GmBh) | Active | 5.000 |
| 21. Emblica (Merck KGaA) | Active | 2.000 |
| 22. Fragrance FAV 22000 (FAV105) | Perfume | 0.300 |
| | | 100% |

Alternative Method of Manufacture of Alternative Composition

This alternative method achieved a change in formulation pH from a pH ranging from 4.0 to 6.5 to a pH ranging from 5.0 to 6.5. Extract of licorice, extract of *bellis perennis* and *emblica* were generally kept under yellow light and/or protected from exposure to white light. In one embodiment, the entire process, including packaging, preferably takes place under yellow light. In another embodiment, the resulting formulation is stored without exposure to white light and air.

Premixes

1. Premix A: In an additional suitable container add Tinosorb M® (Methylene Bis-Benzotriazolyl Tetramethylbutylphenol (and) Decyl Glucoside (and) Xanthan Gum (and) Propylene glycol (and) Water and Purified Water $2^{nd}$ Portion. Agitate until totally dispersed. Reserve.
2. Premix B: In an additional suitable container add DC9040® (Dimethicone Crosspolymer (and) Cyclomethicone and DC5225C® (Cyclopentasiloxane/PEG/PPG-18/18 Dimethicone). Agitate until totally dispersed. Reserve.
3. Premix C: In an additional suitable container add Propylene Glycol and Licorice Extract. Agitate until totally dissolved. Reserve.
4. Premix D: In an additional suitable container add *Emblica* and Purified Water $3^{rd}$ Portion Agitate until totally dispersed. Reserve.
5. Premix E: In an additional suitable container add Triethanolamine 99W and Purified Water $4^{th}$ Portion. Agitate until totally diluted. Reserve.
6. Premix F: In an additional suitable container add Sodium Metabisulfite and Purified Water $5^{th}$ Portion. Agitate until totally dissolved. Reserve.

Preparation of Oily Phase

7. In a suitable container, prepare the Oily Phase adding Cetyl Alcohol, Montanov L® (C14/C22 Alcohol C12/C20 Alkyl Glycoside), Ethylhexyl methoxycinnamate and Butylhydroxytoluene. Heat during agitation to 75° C.±2° C.

Preparation of Aqueous Phase

8. Add Purified Water $1^{st}$ Portion and Disodium EDTA to the principal reactor. Heat to 75° C.±2° C. during agitation and homogenization.

Emulsion

9. When both phases reach 75°±2° C., pour oily phase over the aqueous phase, during intense agitation and homogenization. Check to see if the emulsion formed is homogenous after 15 minutes of homogenization. If necessary, agitate and homogenize for longer time.
10. Cool to 37° C.±2° C.
11. Add Premix D and agitate until completely homogenized.
12. Add Premix E, agitate and homogenize well for at least 15 minutes.
13. Add Premix A under intense agitation.
14. Add Neolone PE® (Phenoxyethanol (and) Methylisothiazolinone), Premix B, Premix C, and Belides® (Extract of *Bellis Perennis*). Agitate and homogenize until smooth.
15. Add Simugel NS® (Hydroxyethyl Acrylate (and) Acryloyldimethyl Copolymer (and) Sodium Taurate (and) Squalane (and) Polysorbate 60) to the main reactor under intense homogenization and incorporate agitation when all the material is in the tank. Agitate and homogenize well for at least 15 minutes.
16. Add Fragrance FAV 22000® and homogenize.
17. Add Premix F, agitate and homogenize well for at least 15 minutes.
18. Collect a sample from the top and from the bottom, measure the pH (range between 5.0 to 6.5). No variation in the results of the pH between the samples should be greater than 0.3 arbitrary pH units, which shows homogeneity. If necessary, continue agitating until the aforementioned parameter is attained.

Screening of Volunteers

1. Population Sampling:

Ten (10) volunteers, of both sexes, of ages between 18 and 60 years old, were screened for the performance of the study. The subjects participating had the first four letters of the name and the first letter of the family name, an individual identification number (generated by electronic system) and a protocol number.

2. Inclusion Criteria:

Age level: 18 to 60 years old;

Phototypes II and III, according to Fitzpatrick's classification;

Whole skin at test site;

Agreement to follow the assay procedures and to come to the clinic at the days and times determined for the evaluations;

Signature of the informed consent form.

3. Exclusion Criteria

Pregnancy or breastfeeding;

Use of anti-inflammatory or immunosuppressant drugs;

Personal precedents of atopy;

Use of topical or systemic photosensitizing medication;

History of phototoxic or photoallergic reactions;

History of sensitization or irritation to topic production;

Photo-induced pathologies, such as sun hives, lupus erythematosus, polyform rash at light, recurring herpes simplex;

Presence of active inflammatory dermatoses at test site;

Presence of nevus lesions at the test site;

Active skin pathologies;

History of sensitization or irritation to topic production;

Frequent exposure to sun or tanning beds;

In use of new innovative drugs within the last 6 months;

Methodology

1. Methodological Procedures:

After the initial procedures, the minimum erythematose dose necessary to induce pigmentation in each volunteer, was determined as described below.

a. Calculation of the Minimum Erythematose Dose:

Each volunteer was subjected to a pre-test to evaluate the minimum erythematose dose (MED). A series of six exposures were applied to the unprotected skin of each volunteer, each one of them being 12% higher than the previous one, in geometric progression. The median dose was previously determined according to Fitzpatrick Phototype, shown in Table I below:

TABLE I

| Type | Color | Sensitivity | Reaction | MED |
|---|---|---|---|---|
| I | White - Pale Light eyes and hair | Very Sensitive | Always burns, never tans | 0.85 |
| II | White | Very Sensitive | Always burns, never tans | 1 |
| III | Darker white | Sensitive | Burns moderately, tans moderately | 1.3 |
| IV | Light brown | Little Sensitive | Burns minimally, always tans | 1.75 |
| V | Brown | Little Sensitive | Burns rarely, always tans | 2.3 |
| VI | Black | Non-Sensitive | Never burns, always pigments | 4.6 |

After irradiation, the volunteers were dismissed and instructed to return after 24 hours. Exposure data was recorded for each volunteer.

b. Reading:

After irradiation, each volunteer was released and instructed to return within 24 hours, whereby the exposure site was read with the volunteer in a vertical position at a predetermined distance and illumination which was kept constant for each volunteer. The MED was then determined for each volunteer.

The individual Minimum Erythematose Dose (iMED) is defined as the minimum ultraviolet (UV) radiation dose necessary to produce clear and well-defined contour erythema at the exposure site, which was used as a reference during the test stage.

Accordingly, sub-sites not presenting erythema were a required criterion for the test evaluation. If this does not occur, new applications must be performed to determine the iMED.

c. Induction of Pigmentation:

After iMED determination, each test site, located on the back, between the pelvic and scapular waist, laterally to the medial line of the spine, was marked with the volunteer in a horizontal position and using a marker. Three sites indicated for the application of the products were delimited, i.e., Site B, Site E, and Site F. Each site was 35 cm² (07×05 cm). At each of the delimited sites, irradiation equivalent to 1.5 times the minimum erythematose dose, previously calculated for each volunteer, was applied. This application was repeated twice whereby each site was irradiated a total of three times.

d. Product Application:

After the irradiation, the volunteers were dismissed and instructed to return after 72 hours for photographic documentation and colorimetric evaluation of the sites. Subjects were tested in triplicate with each of Site B, E, and F corresponding to three distinct irradiation areas to provide a total of three test Sites and nine designation areas per subject. After evaluation, 2 mg of each test material was applied to a designated irradiation area of a test Site on each subject once daily according to the sequence below:

Site B: Hydroquinone 2%;
Site E: The present topical cosmetic composition;
Site F: Negative Control: Site with no product application.

In order to optimize the products permeation and avoid product migration, handling or UV exposure, the product application sites were occluded with filter paper, supported by a semi-permeable adhesive tape. The volunteer returned to the clinic for application, readings and evaluations according to Table II below.

TABLE II

| | Fri T-3 | Mon T0 | Wed T02 | Fri T04 | Mon T07 | Wed T09 | Fri T11 | Mon T14 | Wed T16 | Fri T18 | Mon T21 |
|---|---|---|---|---|---|---|---|---|---|---|---|
| Dermatological Evaluation | X | | | | | | | | | | X |
| Colorimetric evaluation | | X | | | X | | | X | | | X |
| Photographic documentation | | X | | | X | | | X | | | X |
| Reading of irradiated site | X | X | | | | | | | | | |
| Products application | | X | X | X | X | X | X | X | X | X | X |
| UVB irradiation | X | | | | | | | | | | | e. Colorimetric Evaluation:

The colorimetric evaluation was performed using a CHROMA METER. All measurements were performed three times, the L*a*b* parameters average were recorded for each volunteer. The L* parameter was separately statistically analyzed, as its value decreases.

f. Statistics:

To check if there is a statistically significant difference between the treated and control sites and between the experimental timepoints, the parameter L* was compared. This comparison was made through t-student tests for paired data.

Results

The treatments were evaluated clinically and colorimetrically on day T7, T14 and T21. Site B which contained the positive control (Hydroquinone 2%) had the colorimetric average for each experimental time as shown in FIG. 1. FIG. 1 illustrates progressive lightening over time that becomes statistically significant after 21 days. Table III below shows the results of the comparison test between the L* of T0 averages and the other experimental times for area 1 (Site B). Talbe IV shows the raw data for the individual results for the area 1 (Site B) for each volunteer in term of L*, a*, and b* for each of T0, T07, T14, and T21.

TABLE III

| EVALUATED DIFFERENCE | P-VALUE | CONCLUSION* |
|---|---|---|
| T0 and T7 | 0.3626 | Does not reject the hypothesis.** |
| T0 and T14 | 0.1049 | Does not reject the hypothesis. |

TABLE III-continued

| EVALUATED DIFFERENCE | P-VALUE | CONCLUSION* |
|---|---|---|
| T0 and T21 | 0.0182 | Rejects the hypothesis. |

*Level of Significance: 5%
**Hypothesis: there are no differences between the treated area and control area.

TABLE IV

Individual results of the hydroquinone treatment area

| | T0 | | | T07 | | | T14 | | | T21 | | |
|---|---|---|---|---|---|---|---|---|---|---|---|---|
| Vol | L* | a* | b* | L* | a* | b* | L* | a* | b* | L* | a* | b* |
| 1 | 59.9 | 7.53 | 15.73 | 60.01 | 7.42 | 15.69 | 62.03 | 5.93 | 15.68 | 63.76 | 4.85 | 14.48 |
| 2 | 56.0 | 14.38 | 10.40 | 58.96 | 8.98 | 11.06 | 60.53 | 8.28 | 12.11 | 58.87 | 9.17 | 13.64 |
| 3 | 60.1 | 6.66 | 16.34 | 61.44 | 6.39 | 15.55 | 61.74 | 4.86 | 15.25 | 61.8 | 4.71 | 17.09 |
| 4 | 65.74 | 7.13 | 15.32 | 65.15 | 7.63 | 14.16 | 64.97 | 7.93 | 14.44 | 65.32 | 6.47 | 15.01 |
| 5 | 54.45 | 12.42 | 17.88 | 53.77 | 9.90 | 19.02 | 53.77 | 9.90 | 19.02 | 54.39 | 10.55 | 18.22 |
| 6 | 61.36 | 8.21 | 12.76 | 61.74 | 7.53 | 13.82 | 62.44 | 7.00 | 14.40 | 62.79 | 8.74 | 13.08 |
| 7 | 59.06 | 10.74 | 16.83 | 60.01 | 8.24 | 16.84 | 59.68 | 8.19 | 19.00 | 61.74 | 8.18 | 16.55 |
| 8 | 59.16 | 11.14 | 15.70 | 60.07 | 9.80 | 16.17 | 60.95 | 8.91 | 15.96 | 60.96 | 11.34 | 16.72 |
| 9 | 57.67 | 10.24 | 13.93 | 59.62 | 6.99 | 16.36 | 58.58 | 6.76 | 17.54 | 61.44 | 6.63 | 16.14 |
| 10 | 59.92 | 12.78 | 13.45 | 61.26 | 9.01 | 15.86 | 62.00 | 8.00 | 15.53 | 62.91 | 9.74 | 15.37 |

Figure 2:
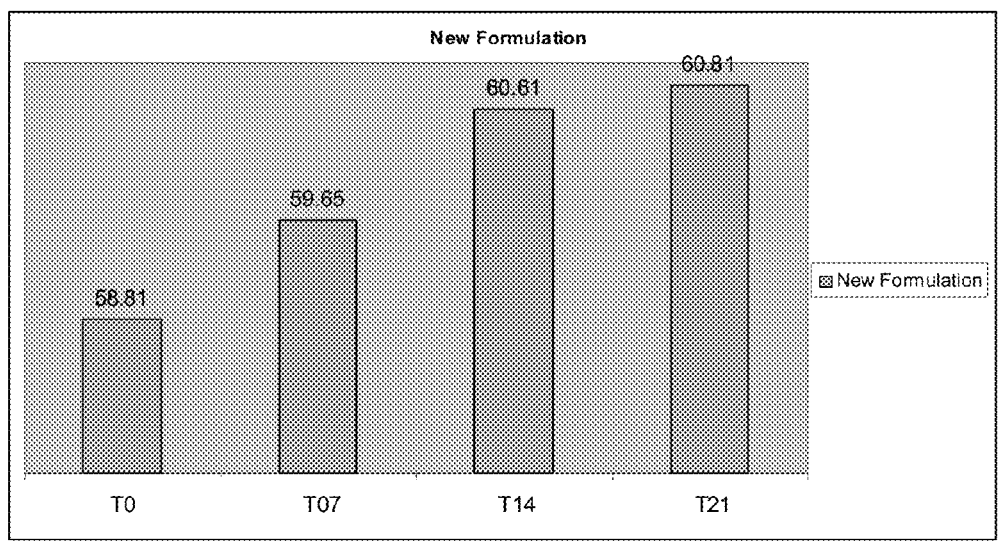
FIG. 2 illustrates progressive lightening over time that becomes statistically significant after 14 days for Site E treated with the present topical cosmetic composition.

FIG. 2 illustrates the results obtained for Site E, i.e., the application location of the evaluated present topical cosmetic composition. FIG. 2 illustrates that there is progressive lightening over time that becomes statistically significant after 14 days. Table V below illustrates the results of the comparison test between the L* of T0 averages and the other experimental times for area 2 (Site E). Table VI shows the raw data for the individual results for area 2 (Site E) for each volunteer in term of L*, a*, and b* for each of T0, T07, T14, and T21.

TABLE V

| EVALUATED DIFFERENCE | P-VALUE | CONCLUSION* |
|---|---|---|
| T0 and T07 | 0.2228 | Does not reject the hypothesis.** |
| T0 and T14 | 0.0022 | Rejects the hypothesis. |
| T0 and T21 | 0.0020 | Rejects the hypothesis. |

*Level of Significance: 5%
**Hypothesis: there are no differences between the treated area and control area.

TABLE VI

Individual results of the present topical cosmetic composition

| | T0 | | | T07 | | | T14 | | | T21 | | |
|---|---|---|---|---|---|---|---|---|---|---|---|---|
| Vol | L* | a* | b* | L* | a* | b* | L* | a* | b* | L* | a* | b* |
| 1 | 58.82 | 10.34 | 14.33 | 61.55 | 6.50 | 14.68 | 62.66 | 7.49 | 13.97 | 64.68 | 4.01 | 15.29 |
| 2 | 55.96 | 15.97 | 11.69 | 57.50 | 8.82 | 10.81 | 59.20 | 9.68 | 12.34 | 60.17 | 8.06 | 12.51 |
| 3 | 61.33 | 7.02 | 16.55 | 61.99 | 6.41 | 15.87 | 61.23 | 5.78 | 15.16 | 62.9 7 | 6.00 | 16.77 |
| 4 | 63.82 | 8.53 | 14.95 | 62.64 | 9.37 | 14.60 | 62.69 | 9.03 | 15.85 | 62.01 | 9.48 | 15.40 |
| 5 | 54.76 | 10.98 | 18.08 | 55.08 | 9.53 | 18.29 | 55.08 | 9.53 | 18.29 | 55.22 | 9.90 | 18.66 |
| 6 | 60.8 9 | 7.76 | 14.01 | 60.64 | 8.61 | 14.83 | 61.81 | 6.78 | 15.30 | 62.32 | 8.39 | 13.50 |
| 7 | 60.34 | 9.17 | 16.28 | 60.69 | 7.98 | 16.54 | 60.27 | 7.03 | 18.05 | 60.67 | 9.09 | 17.34 |

TABLE VI-continued

Individual results of the present topical cosmetic composition

| | T0 | | | T07 | | | T14 | | | T21 | | |
|---|---|---|---|---|---|---|---|---|---|---|---|---|
| Vol | L* | a* | b* | L* | a* | b* | L* | a* | b* | L* | a* | b* |
| 8 | 58.65 | 11.75 | 15.60 | 58.64 | 11.23 | 15.51 | 60.90 | 8.60 | 16.34 | 62.28 | 10.52 | 14.14 |
| 9 | 57.75 | 10.59 | 15.10 | 59.00 | 7.54 | 16.11 | 61.44 | 5.36 | 16.50 | 63.43 | 6.39 | 14.44 |
| 10 | 59.72 | 10.61 | 15.83 | 60.66 | 8.59 | 15.77 | 61.41 | 7.27 | 13.70 | 62.17 | 9.39 | 16.58 |

Figure 3:
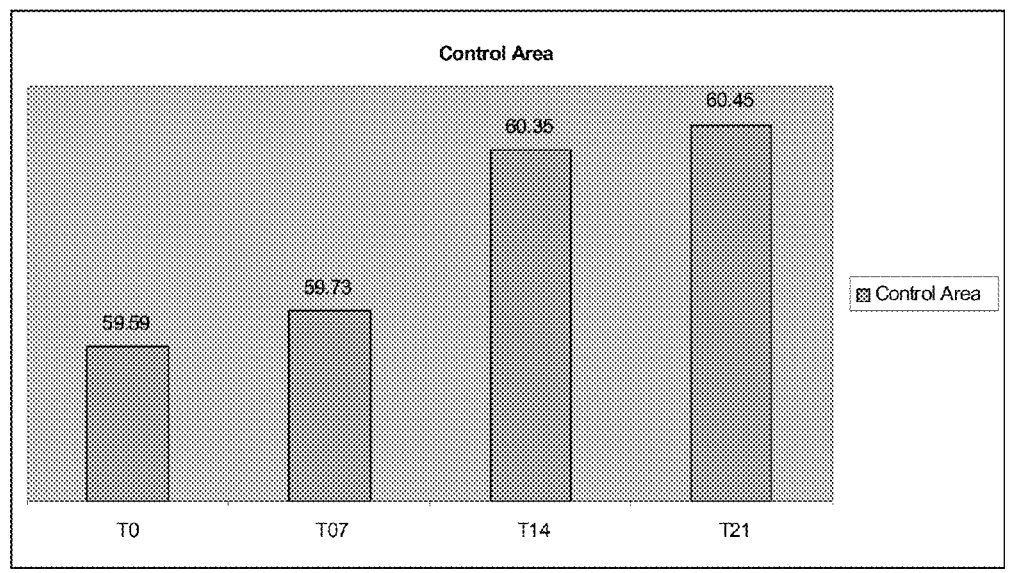
FIG. 3 illustrates progressive lightening (natural degradation of the synthesized melanin), without any significance over the experimental times for the control location (Site F) which was not treated.

FIG. 3 illustrates, for the control location Site F, i.e., where there was no treatment for the irradiation, progressive lightening (natural degradation of the synthesized melanin), without any significance over the experimental times. Table VII below shows the results of the comparilson test between the L* of T0 averages and the other experimental times for the control area (Site F). Table VIII shows the raw data for the individual results for the control area (Site F) for each volunteer in term of L*, a*, and b* for each of T0, T07, T14, and T21.

TABLE VII

| EVALUATED DIFFERENCE | P-VALUE | CONCLUSION* |
|---|---|---|
| T0 and T07 | 0.2220 | Does not reject the hypothesis.** |
| T0 and T14 | 0.2386 | Does not reject the hypothesis. |
| T0 and T21 | 0.2039 | Does not reject the hypothesis. |

*Level of Significance: 5%
**Hypothesis: there are no differences between the treated area and control area.

TABLE VIII

Individual results of the control area

| | T0 | | | T07 | | | T14 | | | T21 | | |
|---|---|---|---|---|---|---|---|---|---|---|---|---|
| Vol | L* | a* | b* | L* | a* | b* | L* | a* | b* | L* | a* | b* |
| 1 | 59.14 | 9.94 | 18.73 | 58.38 | 6.89 | 17.12 | 60.71 | 5.48 | 15.25 | 61.01 | 4.32 | 16.09 |
| 2 | 57.38 | 13.43 | 11.23 | 57.72 | 9.40 | 12.29 | 58.80 | 8.28 | 13.08 | 57.63 | 6.68 | 14.60 |
| 3 | 60.69 | 7.01 | 17.36 | 60.76 | 5.08 | 16.74 | 59.05 | 4.85 | 16.93 | 60.54 | 3.89 | 16.60 |
| 4 | 67.55 | 5.62 | 16.95 | 65.16 | 6.98 | 15.57 | 64.54 | 6.83 | 16.21 | 64.12 | 6.52 | 16.70 |
| 5 | 53.18 | 11.24 | 18.46 | 54.10 | 8.04 | 19.13 | 58.04 | 8.04 | 19.13 | 54.22 | 8.53 | 19.96 |
| 6 | 62.73 | 8.22 | 13.81 | 62.86 | 6.29 | 13.85 | 62.34 | 5.87 | 15.20 | 63.19 | 7.10 | 13.15 |
| 7 | 57.51 | 10.47 | 18.63 | 59.11 | 7.91 | 17.33 | 59.67 | 5.92 | 19.21 | 60.97 | 7.70 | 18.03 |
| 8 | 58.68 | 11.31 | 15.10 | 59.69 | 9.20 | 17.29 | 61.96 | 7.41 | 16.20 | 59.31 | 12.23 | 17.90 |
| 9 | 59.68 | 8.49 | 15.60 | 59.91 | 7.05 | 17.01 | 62.05 | 5.53 | 15.59 | 63.37 | 7.12 | 11.30 |
| 10 | 59.33 | 12.14 | 14.27 | 59.60 | 7.99 | 16.56 | 60.29 | 7.13 | 16.40 | 60.15 | 9.00 | 17.06 |

Figure 4:
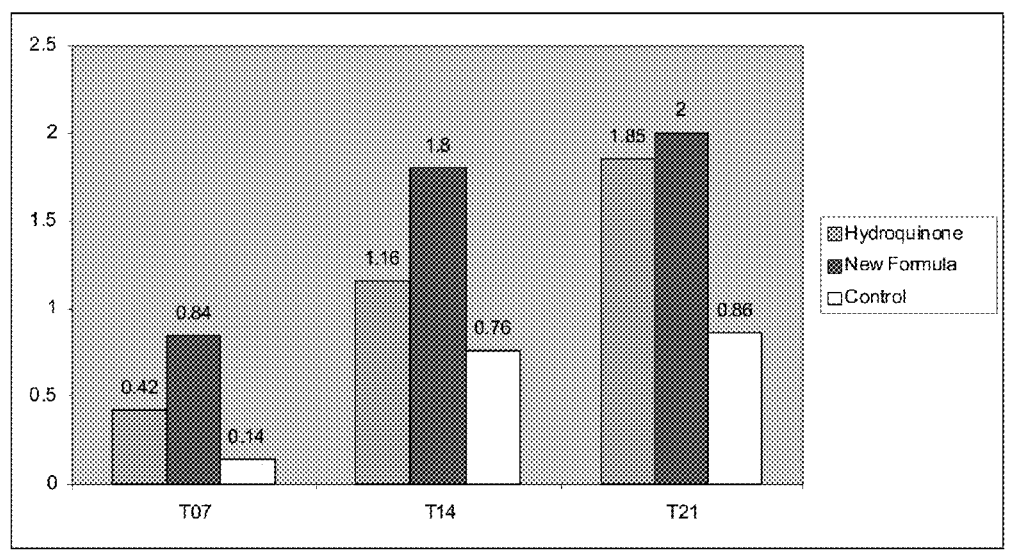
FIG. 4 illustrates the comparison between the averages of the colorimetric values in treatments 1 (Site B) and 2 (Site E) and the control (Site F) over the evaluation times.

FIG. 4 illustrates the comparison between the averages of the colorimetric values in treatments 1 and 2 and the control over the evaluation times. Table IX illustrates that only the present topical cosmetic formulation exhibited statistically significant reduction in pigmentation as compared to the spontaneous reduction in pigmentation observed in the control group.

TABLE IX

| EVALUATED DIFFERENCE | P-VALUE | CONCLUSION* |
|---|---|---|
| New formulation and Hydroquinone | 0.13 | Does not reject the hypothesis.** |
| New formulation and Control | 0.02 | Rejects the hypothesis. |
| Hydroquinone and Control | 0.10 | Does not reject the hypothesis.**tks |

*Level of Significance: 5%
**Hypothesis: there are no differences between the areas.

Discussion

In an experimental model with UV radiation induced pigmentation (melanogenesis) and having no preexisting pigmentary dysfunction, clinical pigmentation will be reduced spontaneously over time, on the treated areas. All locations, including the untreated control, exhibited a significant reduction in pigmentation up to T21 as evaluated using a colorimeter.

Therefore, this experiment was carried out to comparatively evaluate which treatments would cause the quickest and most significant depigmentation. Because all of the treatments were applied simultaneously to each volunteer, the variable of melanization capacity was significantly reduced. Accordingly, depigmentation would occur at the same speed on all of the tested locations, in each volunteer.

Starting from this premise, the lightening effect was clinically observed over time for each location, which has already allowed for a visual evaluation and a comparative analysis.

To improve the accuracy of these observations and to allow for objective, consistent, and reproducible evaluation, the colorimeter was used as a complementary instrumental evaluation, enabling the detection of differences which the human eye cannot detect.

According to the colorimetry, the L* parameter provided by the colorimetric measurement is the index directly related to the skin's luminosity. The higher the value of L* the lighter the evaluated region.

Clinically and colorimetrically evaluating the treatments the progressive depigmentation was expected, as it deals with an experimental melanization phenomenon. The irradiated but untreated control locations, presented a significant colorimetric improvement of L* as from T21, with the hydroquinone; nevertheless, the lightening levels, when compared to the hydroquinone on T07 and T14, were statistically lower.

Still considering the data over time, the results differ in the following manner: Hydroquinone: significantly improves as from T21; The present topical cosmetic composition: significantly improves as from T14, with statistically significant higher lightening levels when compared to the control. Accordingly, the present topical cosmetic composition provided a faster and more significant lightening effect (provides a higher lightening index) as compared to hydroquinone.

Figure 5:
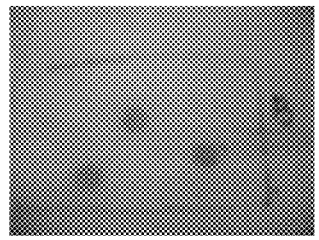
FIG. 5 illustrates photographs of clinical data supporting the colorimetric results in treatments 1 (Site B) and 2 (Site E) and the control (Site F) comparing evaluation times T0 and T21.
Figure 5:
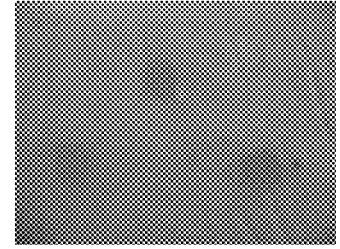
Figure 5:
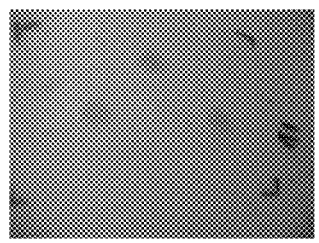
Figure 5:
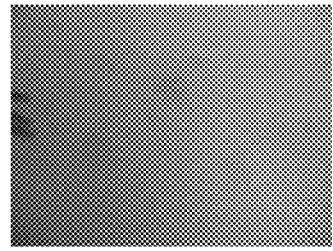
Figure 5:
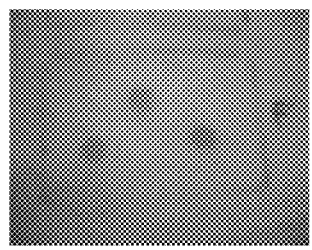
Figure 5:
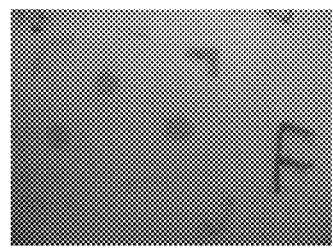

FIG. 5 shows photographs of clinical data supporting the colorimetric results, where the greater average lightening effect was obtained on the location with the new formula. The hydroquinone treatment and the new formulation were similar at the end of the study, although the new formulation is faster and provides a higher lightening index.

Example 2

The following example illustrates the preparation of a cream in accordance with the presently described subject matter:

| Component | Function | % W/W |
| --- | --- | --- |
| Purified water | carrier | 62.250 |
| Cetyl alcohol | thickening agent | 2 |
| Xanthan gum | thickening agent | .2 |
| Butylated hydroxytoluene | antioxidant | .050 |
| C14-22 alcohols and C12-20 alkylglucoside | emulsifier | 2 |
| Potassium cetyl phosphate | emulsifier | 1 |
| Glyceryl stearate and PEG-100 stearate | emulsifier | 2 |
| Cyclomethicone | emollient | 2 |
| Disodium edetate | chelating agent | .2 |
| Bellis perennis flower extract | antioxidant/active | 5 |
| Phyllanthus Embilica Fruit Extract | antioxidant/active | 2 |
| Licorice extract | antioxidant/active | .050 |
| Phenoxyethanol and methylisothiazolinone | preservative | .6 |
| Perfume FAV22000-Essential Oils Blend | fragrance | .3 |
| Hydroxyethyl acrylate, Sodium acryloyldimethyltaurate copolymer, Squalane, and Polysorbate 60 | thickening agent | 5 |
| Sodium metabissulfite | antioxidant | .3 |
| Methylene bis-benzotriazolyl tetramethylphenol | sunscreen active | 5 |
| Ethylhexyl Methoxycinnamate | sunscreen active | 7.5 |
| Propylene Glycol | emollient | 2 |
| Triethanolamine | pH adjuster | .55 |
| | | 100.0% |

The composition is prepared as in Example 1. More specifically, after Premix E is added to the emulsion, Neolone PE (Phenoxiethanol and Methylisothiazolinone) and cyclomethicone are added under high shearing homogenization and mixing for about 15 minutes. The thickening agents including xanthan gum are added in the oil phase.

Example 3

The following example illustrates the preparation of a cream in accordance with the presently described subject matter:

| Component | Function | % W/W |
| --- | --- | --- |
| Purified water | carrier | 63.43 |
| Butylated hydroxytoluene | antioxidant | 0.05 |
| Disodium edetate | chelating agent | 0.20 |
| Propylene glycol | emollient | 2.00 |
| Phyllanthus embilica fruit extract | antioxidant/active | 2.00 |
| Hydroxyethyl acrylate, Sodium acryloyldimethyltaurate copolymer, Squalane, and Polysorbate 60 | thickening agent | 5.00 |
| Methylene bis-benzotriazolyl tetramethylphenol | sunscreen active | 5.00 |
| Bellis perennis extract | antioxidant/active | 5.00 |
| Cyclopentasiloxane dimethicone crosspolymer | emollient | 2.00 |
| Cyclopentasiloxane PEG/PPG-18/18 dimethicone | emollient | 2.00 |
| Phenoxyethanol and methylisothiazolinone | preservative | 0.60 |
| Triethanolamine | pH adjuster | 0.57 |
| Perfume | perfume | 0.30 |
| Cetyl alcohol | thickening agent | 2.00 |
| C14-22 alcohols and C12-20 alkylglucoside | emulsifier | 2.00 |
| Ethylhexyl methoxycinnamate | sunscreen active | 7.50 |
| Sodium metabissulfite | antioxidant | 0.30 |
| Licorice extract | antioxidant/active | 0.05 |
| | | 100.0% |

The composition was prepared as in Example 1.

Example 4

The following example illustrates a generally applicable method for administering a composition in accordance with the presently described subject matter:

A topical cosmetic composition is administered topically to the skin of a subject being treated by conventional means. This is preferably done through the use of a serum or cream gel formulation. A topical preparation may thus be applied to the desired skin surface area with, for example, the use of the fingertips.

For topical administration of the cosmetic composition, the subject should be told to first clean the affected area gently and to pat it dry. The topical cosmetic composition may then be applied directly to the affected skin area or dispensed into the palm of the hand or suitable vessel from which material may be taken and manually applied to the skin area to be treated.

Example 5

A subject is suffering from undesired skin pigmentation. A topical cosmetic composition as described herein is topically administered to undesirably pigmented areas of the skin of the subject. It would be expected that the undesirably pigmented areas of the skin of the subject would be lightened.

Example 6

A subject is suffering from vitiligo. A topical cosmetic composition as described herein is topically administered to the residual areas of normal skin of the subject. It would be expected that the residual areas of normal skin of the subject would be lightened to impart a homogeneous color to the entire skin.

Example 7

A subject is suffering from age spots. A topical cosmetic composition as described herein is topically administered to the affected skin areas of the subject. It would be expected that the age spots would be lightened.

All publications cited in the specification are indicative of the level of skill of those skilled in the art to which the presently described subject matter pertains. All of these publications are hereby incorporated by reference herein to the same extent as if each individual publication were specifically and individually indicated as being incorporated by reference.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A topical cosmetic composition, comprising:
   a) a skin lightening component consisting of
      a *Phyllanthus* extract;
      a *Bellis* extract; and
      a licorice extract;
   b) at least one non-skin lightening agent, non-plant derived, selected from
      i) an anti-acne agent,
      ii) an anti-microbial agent,
      iii) an anti-fungal agent,
      iv) an anti-wrinkle agent,
      v) an anti-atrophy agent,
      vi) an anti-inflammatory agent,
      vii) a keratolytic agent,
      viii) a peptide,
      ix) a fatty acid derivative,
      x) a sunscreen,
      xi) an optical brightener, and combinations thereof; and
   c) at least one cosmetically acceptable carrier or excipient, wherein the composition is provided in a topical delivery system selected from the group consisting of a serum, a lotion, a cream, an ointment, a gel, an aerosol, a foam, a foamable liquid, an emulsion, a skin cleaner, a milk, a mask, and a solid stick.

2. The topical cosmetic composition of claim 1, wherein the *Phyllanthus* extract comprises a *Phyllanthus embilica* extract, the *Bellis* extract comprises a *Bellis perennis* extract and the licorice extract comprises a licorice root extract.

3. The topical cosmetic composition of claim 2, wherein the *Phyllanthus embilica* extract is present in an amount of from about 0.25 wt % to about 4 wt %; the *Bellis perennis* extract is present in an amount of from about 1 wt % to about 20 wt %; and the licorice extract is present in an amount of from about 0.01 wt % to about 1 wt %, based on the total weight of the composition.

4. The topical cosmetic composition according to claim 2, wherein the at least one cosmetically acceptable carrier is selected from the group consisting of distilled water, saline, Ringer's solution, dextrose solution, Hanks solution and DMSO.

5. The topical cosmetic composition according to claim 2, wherein the at least one cosmetically acceptable excipient is selected from the group consisting of an antioxidant, a chelating agent, a pH adjuster, an emollient, a thickening agent, a gelling agent, a free radical scavenger, a preservative, an emulsifier, a humectant, a moisturizer, a suspending agent, a surfactant, a stabilizer, a vitamin, a penetration enhancer, a perfume or fragrance, a coloring agent, a fluid alkyl alcohol, a polysiloxane, a modified polysiloxane and combinations thereof.

6. The topical cosmetic composition according to claim 2, wherein the non-skin lightening agent, non-plant derived agent is a sunscreen.

7. The topical cosmetic composition according to claim 6, wherein the sunscreen is present in an amount of from about 0.5 wt % to 30 wt %, based on the total weight of the topical cosmetic composition.

8. The topical cosmetic composition according to claim 7, wherein the sunscreen comprises:
   a first sunscreen selected from the group consisting of methylene bis-benzotriazolyl tetramethylbutylphenol, diethylamino hydroxybenzoyl hexyl benzoate, coated zinc oxide, ethylhexyl methoxycinnamate, isoamyl methoxycinnamate, homosalate, ethyl hexyl salicylate, octocrylene, polysilicone-15, butyl methoxydibenzoylmethane, methyl anthranilate, and ethylhexyl dimethyl PABA and combinations thereof.

9. The topical cosmetic composition according to claim 8, wherein the composition comprises a second sunscreen selected from the group consisting of ethylhexyl methoxycinnamate, isoamyl methoxycinnamate, homosalate, ethyl hexyl salicylate, octocrylene, polysilicone-15, butyl methoxydibenzoylmethane, menthyl anthranilate, ethylhexyl dimethyl PABA, and combinations thereof.

10. The topical cosmetic composition according to claim 9, wherein the first sunscreen is present in an amount of from about 1 wt % to 20 wt %, and the second sunscreen is present in an amount of from about 1 wt % to about 10 wt %, based on the total weight of the topical cosmetic composition.

11. The topical cosmetic composition according to claim 9, wherein the first sunscreen is methylene bis-benzotriazolyl tetramethylphenol, and the second sunscreen is ethylhexyl methoxycinnamate.

12. The composition according to claim 9, wherein the sunscreen in the composition provides for an SPF of greater than about 10.

13. The topical cosmetic composition according to claim 1, wherein the carrier is water.

14. The topical cosmetic composition according to claim 13, wherein the water is present in an amount of from about 3 wt % to about 95 wt %, based on the total weight of the composition.

15. The topical composition according to claim 1 which is a cream, a gel, a serum, or a lotion.

16. The topical composition according to claim 5 wherein the composition comprises as an excipient a thickening agent, an antioxidant, a surfactant, a chelating agent, an emollient, a preservative and a pH adjuster.

17. A method of lightening skin pigmentation in a subject, comprising topically administering to skin of a subject in need thereof, a therapeutically effective amount of the topical cosmetic composition of claim 1.

* * * * *